US007276485B1

(12) United States Patent
Cerreta et al.

(10) Patent No.: US 7,276,485 B1
(45) Date of Patent: Oct. 2, 2007

(54) FLOWABLE NONDIGESTIBLE OIL AND PROCESS FOR MAKING

(75) Inventors: Michael Kenneth Cerreta, Newtown, CT (US); Peter Yau-Tak Lin, Middletown, OH (US); Penelope Marie Edwards, Greendale, IN (US); Mark Lewis Agerton, Fairfield, OH (US)

(73) Assignee: The Procter + Gamble Co., Cincinnati, OH (US)

( * ) Notice: Subject to any disclaimer, the term of this patent is extended or adjusted under 35 U.S.C. 154(b) by 792 days.

(21) Appl. No.: 08/914,743

(22) Filed: Aug. 19, 1997

Related U.S. Application Data

(63) Continuation-in-part of application No. 08/844,590, filed on Apr. 21, 1997, now abandoned.

(51) Int. Cl.
*A61K 31/70* (2006.01)
*A61K 31/715* (2006.01)
*C07H 13/02*

(52) U.S. Cl. .................. 514/23; 536/115; 536/119; 536/124; 514/53; 562/606; 554/1

(58) Field of Classification Search .............. 536/119, 536/124, 115; 514/23, 53; 562/606; 554/1
See application file for complete search history.

(56) References Cited

U.S. PATENT DOCUMENTS

| | | | |
|---|---|---|---|
| 2,482,761 | A | 9/1949 | Goebel |
| 2,731,481 | A | 1/1956 | Harrison et al. |

(Continued)

FOREIGN PATENT DOCUMENTS

| | | |
|---|---|---|
| EP | 0 322 027 | 6/1989 |
| EP | 0 325 010 | 7/1989 |
| EP | 0 375 027 | 6/1990 |
| EP | 0 571 219 | 11/1993 |
| EP | 0 667 105 | 8/1995 |
| WO | WO 92/18015 | 10/1992 |
| WO | WO 93/00823 | 1/1993 |
| WO | WO 94/09638 | 5/1994 |
| WO | WO 94/09641 | 5/1994 |
| WO | WO 97/22260 | 6/1997 |
| WO | WO 98/52428 | 11/1998 |
| WO | WO 98/52429 | 11/1998 |

OTHER PUBLICATIONS

J. Amer. Oil Chem. Soc., vol 55 (1978), pp. 328-331.
Hoffman, Robert—The Modulation Contrast Microscope: Principles and Performances, Journal of Microscopy, vol. 110, Pt 3, Aug. 1977, pp. 205-222.

*Primary Examiner*—James O. Wilson
*Assistant Examiner*—Everett White
(74) *Attorney, Agent, or Firm*—Carl J. Roof

(57) ABSTRACT

A flowable nondigestible oil composition having a Consistency in a temperature range of 20° C. to 40° C. of less than about 600 P.sec$^{(n-1)}$. The flowable nondigestible oil contains a liquid polyol polyester having a complete melt point less than 37° C., and a solid polyol polyester having a complete melt point of at least about 37° C., wherein the solid polyol polyester contains a solid saturated polyol polyester capable of forming crystallized spherulites. The flowable nondigestible oil is made by a process which includes the steps of melting completely the nondigestible oil, reducing the temperature of the melted nondigestible oil to a first crystallization temperature less than the onset crystallization temperature of the solid saturated polyol polyester, holding the nondigestible oil at the first crystallization temperature for a time sufficient to crystallize a portion of the solid saturated polyol polyester into crystallized spherulites, further reducing the temperature to an ambient crystallization temperature, and holding the polyol polyester composition for a time sufficient to crystallize the remaining portion of the solid polyol fatty acid polyester. The process is accompanied by shearing of the composition during the crystallization of the remaining portion of the solid polyol fatty acid polyester. The process is generally completed within 5 hours, usually within about 2 hours.

33 Claims, 3 Drawing Sheets

U.S. PATENT DOCUMENTS

| | | |
|---|---|---|
| 2,793,219 A | 5/1957 | Barrett et al. |
| 2,831,854 A | 4/1958 | Tucker et al. |
| 2,962,419 A | 11/1960 | Westfield |
| 3,353,967 A | 11/1967 | Lutton |
| 3,579,548 A | 5/1971 | Whyte |
| 3,600,186 A | 8/1971 | Mattson et al. |
| 3,914,452 A | 10/1975 | Norris ............... 426/549 |
| 3,932,532 A | 1/1976 | Hunter et al. |
| 3,943,259 A | 3/1976 | Norris ............... 426/24 |
| 3,963,699 A | 6/1976 | Rizzi et al. |
| 4,005,195 A | 1/1977 | Jandacek |
| 4,034,083 A | 7/1977 | Mattson |
| 4,234,606 A | 11/1980 | Gawrilow ............ 426/24 |
| 4,239,786 A | 12/1980 | Gilmore et al. ......... 426/601 |
| 4,335,157 A | 6/1982 | Varvil ............... 426/24 |
| 4,359,482 A | 11/1982 | Crosby .............. 426/606 |
| 4,368,213 A | 1/1983 | Hollenbach et al. |
| 4,391,838 A | 7/1983 | Pate ................. 426/606 |
| 4,455,333 A | 6/1984 | Hong et al. |
| 4,461,782 A | 7/1984 | Robbins et al. |
| 4,508,746 A | 4/1985 | Hamm |
| 4,517,360 A | 5/1985 | Volpenhein |
| 4,518,772 A | 5/1985 | Volpenhein |
| 4,582,715 A | 4/1986 | Volpenhein |
| 4,582,927 A | 4/1986 | Fulcher |
| 4,797,300 A | 1/1989 | Jandacek et al. |
| 4,840,815 A | 6/1989 | Meyer et al. |
| 4,861,613 A | 8/1989 | White et al. |
| 4,888,195 A | 12/1989 | Huhn et al. |
| 4,961,951 A | 10/1990 | Crosby ............... 426/602 |
| 4,983,329 A | 1/1991 | Cooper |
| 5,175,323 A | 12/1992 | Cooper |
| 5,211,981 A | 5/1993 | Purves et al. |
| 5,236,733 A | 8/1993 | Zimmerman et al. ...... 426/611 |
| 5,268,191 A | 12/1993 | Crosby ............... 426/606 |
| 5,273,772 A | 12/1993 | Cooper |
| 5,288,884 A | 2/1994 | Cooper |
| 5,298,637 A | 3/1994 | Cooper |
| 5,304,665 A | 4/1994 | Cooper et al. |
| 5,306,514 A | 4/1994 | Letton et al. ............. 426/531 |
| 5,306,515 A | 4/1994 | Letton et al. ............. 426/531 |
| 5,362,894 A | 11/1994 | Handwerker et al. |
| 5,374,446 A | 12/1994 | Ferenz et al. |
| 5,387,429 A | 2/1995 | Cooper |
| 5,399,728 A | 3/1995 | Cooper |
| 5,399,729 A | 3/1995 | Cooper et al. |
| 5,419,925 A | 5/1995 | Seiden et al. ............. 426/611 |
| 5,422,131 A | 6/1995 | Elsen et al. ............. 426/531 |
| 5,427,815 A | 6/1995 | Ferenz |
| 5,451,416 A | 9/1995 | Johnston et al. ........... 426/531 |
| 5,466,843 A | 11/1995 | Cooper |
| 5,512,313 A | 4/1996 | Cooper et al. |
| 5,516,544 A | 5/1996 | Sekula et al. |
| 5,589,217 A | 12/1996 | Mazurek |
| 5,597,605 A | 1/1997 | Mazurek |
| 5,603,978 A | 2/1997 | White et al. |
| 5,641,534 A | 6/1997 | White et al. |
| 6,518,226 B2 | 2/2003 | Volker et al. |
| 6,562,394 B1 | 5/2003 | Volker |

FLOWABLE NONDIGESTIBLE OIL AND PROCESS FOR MAKING

CROSS-REFERENCED TO RELATED APPLICATIONS

This application is a Continuation-in-Part of application Ser. No. 08/844,590, filed Apr. 21, 1997 now abandoned.

FIELD OF THE INVENTION

This invention relates to a nondigestible oil containing a solid at ambient temperature which can flow at ordinary and ambient storage temperatures, and to a process for making the flowable nondigestible oil.

BACKGROUND ART

Numerous patents have been directed to providing materials which have the physical and gustatory characteristics of triglyceride fats, but which are absorbed to a low extent or not at all by the body. These materials are referred to variously as noncaloric fats, pseudofats, nondigestible fats and fat substitutes. Patents pertaining to such materials include U.S. Pat. No. 4,582,927, Fulcher, issued Apr. 15, 1986, (fatty esters of malonic acid); U.S. Pat. No. 4,582,715, Volpenhein, issued Apr. 15, 1986, (alpha acetylated triglycerides); and U.S. Pat. No. 3,579,548, Whyte, issued May 18, 1981, (triglycerides of alpha-branched chain carboxylic acids).

One particular type of compound which has achieved considerable attention as a nondigestible fat is sucrose polyester (i.e., sucrose in which at least four of the eight hydroxyl groups are esterified with a fatty acid). U.S. Pat. Nos. 3,600,186, Mattson, issued Aug. 17, 1971; 4,368,213, Hollenbach et al. issued Jan. 11, 1983; and 4,461,782, Robbins et al. issued Jul. 24, 1984 describe the use of this material as a nondigestible fat in a variety of food compositions.

A problem associated with use of liquid nondigestible oils, i.e., those having a melting point below body temperature (about 37° C.), is an undesired passive oil loss effect, which is manifested in leakage of the liquid nondigested fat through the gastrointestinal tract's anal sphincter. Regular ingestion of moderate to high levels of completely liquid forms of these polyol polyesters can produce this passive oil loss. U.S. Pat. No. 4,005,195, Jandacek, issued Jan. 25, 1977, discloses the combining of higher melting fatty materials such as solid triglycerides and solid sucrose polyesters with the liquid sucrose polyesters in order to control oil loss.

U.S. Pat. No. 4,797,300 (Jandacek et al.), issued Jan. 10, 1989 discloses the use of certain solid sucrose polyesters which have high oil binding capacity for liquid sucrose polyesters (SPE) and liquid triglycerides, when used at levels of about 10% to 25% in said oils. It is disclosed that because of their high oil binding capacity, these solid sucrose polyesters have outstanding utility as agents to prevent passive oil loss of liquid nondigestible sucrose polyesters, and they are also useful as non-caloric hardstocks to use with liquid digestible or nondigestible oils in the preparation of semi-solid fat products such as shortenings and margarines. The oil binding agents of the Jandacek et al. '300 patent are solid sucrose polyesters wherein the ester groups consist essentially of a mixture of short chain saturated fatty acid ester radicals ($C_2$-$C_{10}$) and long chain saturated fatty acid radicals ($C_{20}$-$C_{24}$) in a molar ratio of short chain to long chain of from about 3:5 to about 5:3, and wherein the degree of esterification is from about 7 to about 8. Jandacek et al. also disclose plastic shortening and other food compositions containing 10-25% of the solid SPE.

U.S. Pat. No. 4,005,195 (Jandacek), issued Jan. 25, 1977 describes a means of preventing the undesirable oil loss effect through the addition of the polyesters as oil-loss control agents. The oil-loss control agents include solid fatty acids (melting point 37° C. or higher) and their triglyceride sources, and solid polyol fatty acid polyesters. Specifically $C_{10}$-$C_{22}$ saturated fatty acid polyesters are said to be useful at levels of at least 10%, preferably at least 20%.

U.S. Pat. No. 5,306,514 (Letton et al.), issued Apr. 26, 1994, discloses edible oil compositions containing a) a liquid nondigestible oil having a complete melting point below about 37° C., and b) a solid polyol fatty acid polyester having a complete melting point above about 37° C., wherein the weight ratio of b) to a) is from about 1:99 to about 9:91. The solid polyol fatty acid polyester consists of (i) a polyol having at least about 4 hydroxyl groups, wherein at least about 4 of the hydroxyl groups of the polyol are esterified, and (ii) ester groups comprised of (a) fatty acid radicals selected from the group consisting of $C_{12}$ or higher unsaturated fatty acid radicals, $C_2$-$C_{12}$ saturated fatty acid radicals, or mixtures thereof, and (b) $C_{20}$ or higher saturated fatty acid radicals, at a molar ratio of (a):(b) being from about 1:15 to about 1:1. In the solid polyol polyester at least 15% by weight of the fatty acid radicals are $C_{20}$ or higher saturated fatty acid radicals. Further, the slope of the SFC profile of the mixture of a) and b) between 37° C. and 21.1° C. is between 0 and about −0.75.

U.S. Pat. No. 5,306,515 (Letton et al.), issued Apr. 26, 1994, discloses pourable compositions containing (A) a solid polyol fatty acid polyester, having a complete melting point above about 37° C., (B) a liquid nondigestible oil having a complete melting point below about 37° C., less than about 90% by weight of a digestible oil having less than 5% solids at 21° C.; and less than 10% hardstock; wherein the ratio of (A) to (B) is from about 1:99 to about 9:91 and wherein the pourable composition has a yield point of not more than about 100 dynes/cm². The solid polyol fatty acid polyester consists of (i) a polyol having at least about 4 hydroxyl groups, wherein at least about 4 of the hydroxyl groups of the polyol are esterified, and (ii) ester groups comprised of (a) fatty acid radicals selected from the group consisting of $C_{12}$ or higher unsaturated fatty acid radicals, $C_2$-$C_{12}$ saturated fatty acid radicals or mixtures thereof, and (b) $C_{20}$ or higher saturated fatty acid radicals at a molar ratio of (a):(b) being from about 1:15 to about 2:1. In the solid polyol polyester at least 15% by weight of the fatty acid radicals are $C_{20}$ or higher saturated fatty acid radicals. Further, the slope of the SFC profile of the mixture of (A) and (B) between 37° C. and 21.1° C. is between 0 and about −0.75, and the combined level of (A) and (B) in said composition is at least 10% by weight. Examples include compositions containing 65 wt. % liquid digestible triglyceride oil.

It is an object of the present invention to provide a flowable nondigestible oil composition containing a solid at ambient temperature which is flowable at ordinary and ambient temperatures, and which can subsequently be used as an edible nondigestible oil providing good passive oil loss control and good organoleptic properties to foods prepared with them.

SUMMARY OF THE INVENTION

A flowable nondigestible oil composition of the present invention comprises a) a liquid polyol fatty acid polyester having a complete melt point less than 37° C., and b) a solid polyol fatty acid polyester having a complete melt point of at least about 37° C. The flowable nondigestible oil has a Consistency (K) within the temperature range of 20-40° C. of less than about 600 P.sec$^{(n-1)}$, where K is determined from a power law model fit of the apparent viscosity versus shear rate data (see Analytical Method Section), and n is the shear index (dimensionless). Preferably, the flowable nondigestible oil has a Consistency of less than about 400 P.sec$^{(n-1)}$ at a temperature range of 20-40° C. The flowable nondigestible oil composition contains the solid polyol fatty acid polyester in the crystallized form of spherulites, unaggregated platelets, aggregate particles, and combinations and mixtures thereof.

The present invention also provides a process for making a flowable nondigestible oil, wherein the nondigestible oil comprises a) a liquid polyol fatty acid polyester having a complete melt point less than 37° C., and b) a solid polyol fatty acid polyester having a complete melt point of at least about 37° C., the solid polyol fatty acid polyester comprising a solid saturated polyol polyester which is capable of crystallizing into spherulites. The process comprises the steps of melting completely the nondigestible oil composition containing the solid polyol fatty acid polyester, crystallizing a portion of the solid saturated polyol polyester into a plurality of spherulites, thereby forming a partially crystallized polyol polyester composition, and further crystallizing a remaining portion of the solid polyol fatty acid polyester, thereby forming the flowable nondigestible oil composition.

These compositions are capable of being stored in a flowable state at ambient and ordinary storage temperatures. Storage at ambient and ordinary temperature avoids exposure of the composition to high temperatures (generally greater than 50° C.) usually associated with storage and handling of the nondigestible oil composition in a molten form. Making and storing the nondigestible oil in a flowable form allows the nondigestible oil to be easily handled at ambient handling and storage temperatures, which minimizes the effect of heat and high temperature on the chemical stability of the polyol fatty acid polyester. This results in greater oxidative and flavor stability during extended storage of the nondigestible oil and of food products containing the nondigestible oil. This is particularly advantageous when the liquid polyol fatty acid polyester component of the nondigestible oil is made from an unhardened (non-hydrogenated) source oil, such as unhardened cottonseed oil. In addition, the flowable nondigestible oil of the present invention can be utilized as a carrier for the application or incorporation of ingredients to foods products, such as flavorings, seasonings, and vitamins.

DEFINITIONS

As used herein the term "nondigestible" shall mean being absorbable to an extent of only 70% or less (especially 20% or less) by the human body through its digestive system.

As used herein, the term "flowable" refers to ability of a composition to be transported by gravity or by conventional mechanical or pneumatic pumping means from a storage vessel.

As used herein the term "ambient" shall mean a temperature which is less than the lowest onset crystallization temperature of a solid polyol fatty acid polyester in the nondigestible oil composition.

As used herein, the term "food" refers to any manner of viand for usage by man. "Food" may further include individual food components or mixtures thereof.

As used herein, the term "comprising" means various components can be conjointly employed in the fat compositions of the present invention. Accordingly, the term "comprising" encompasses the more restrictive terms "consisting essentially of" and "consisting of".

All percentages and proportions herein are by weight unless otherwise specified.

DETAILED DESCRIPTION OF THE INVENTION

Figure 1A:
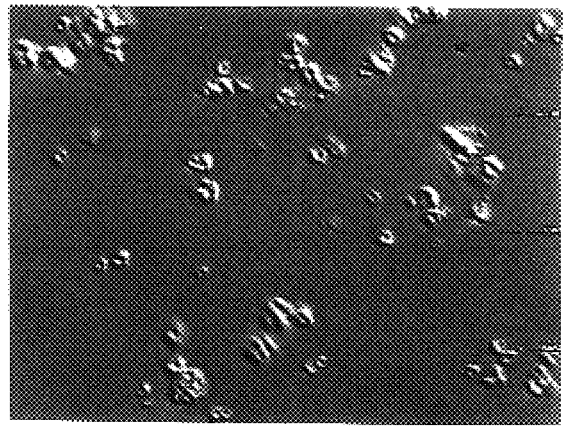
FIGS. 1a through 1d are photomicrographs (magnification 1000x) depicting spherulite particles of solid saturated sucrose polyester dispersed in a liquid sucrose polyester at total solid levels of 1%, 3%, 6%, and 9%, by weight, respectively.

High temperatures and exposure to oxygen can result in thermal and oxidative decomposition of the nondigestible oil composition. It is preferred to avoid storage and handling of the nondigestible oil at the higher temperatures provided in heated railway cars and production tanks, which are needed to maintain the nondigestible oil in a molten state.

Consequently, there is a significant advantage to store and transport the nondigestible oil at lower, ambient temperatures, and in the absence of oxygen, to inhibit or reduce thermal and oxidative degradation of the nondigestible oil composition, to improve the quality of the nondigestible oil composition and the foods prepared therewith, and to require less expensive and less complicated transportation and storage requirements for the nondigestible oil composition. Generally, the ambient temperature at which the flowable nondigestible oil of the present invention would be stored is from about 5° C. to about 50° C., and more preferably from about 20° C. to about 40° C.

To commercially process the nondigestible oil economically and in large quantities, there is a need for a rapid process to make a flowable nondigestible oil composition which can be handled and stored at ambient temperature. Preferably such a process would convert the nondigestible oil into a flowable nondigestible oil at ambient conditions in less than 2 hours, and more preferably in less than one hour. For commercial reasons, the flowable nondigestible oil composition of the present invention should have good flow properties, such that the flowable nondigestible oil will drain sufficiently, preferably substantially completely, by the force of gravity from the inside of transportation vessels, such as railway cars, and manufacturing containers, such as tanks. Preferably, the flowable nondigestible oil composition of the present invention generally will not adhere in a mass to the side walls and other surfaces inside the trucks, railway cars or tanks. That is, the flowable nondigestible oil will typically drain such that only a relatively thin layer or film of the nondigestible oil will remain on the inside surfaces of a vessel or tank. Preferably, the flowable nondigestible oil is stable during extended storage; i.e., it remains flowable and there is minimal and preferably no separation or settling of the solid crystals.

A. Composition of Flowable Nondigestible Oil

A flowable nondigestible oil composition comprising a solid polyol fatty acid polyester having a complete melting point of at least about 37° C. and a liquid polyol polyester having a complete melting point of less than about 37° C., can be prepared which is flowable at ambient storage temperatures, and can, upon further processing including remelting completely the solid polyol fatty acid polyester, provide good passive oil loss control and organoleptic properties (i.e. good mouthfeel) to foods prepared therewith. The flowable nondigestible oil composition of the present invention generally comprises about 50% to about 99%, more preferably about 80% to 97%, and most preferably about 85% to 95%, of the liquid polyol fatty acid polyester. The flowable nondigestible oil composition of the present invention generally comprises about 1% to 50%, more preferably about 3% to 20%, and most preferably about 5% to 15%, of the solid polyol fatty acid polyester.

The flowable nondigestible oil composition generally has a Consistency of less than 600 $P.sec^{(n-1)}$ in a temperature range of from 20-40° C. The flowable nondigestible oil composition will have a Consistency of preferably less than about 400 $P.sec^{(n-1)}$, more preferably less than about 200 $P.sec^{(n-1)}$, and most preferably less than about 100 $P.sec^{(n-1)}$, in a temperature range of 20-40° C.

Mixtures of solid polyol polyesters of the invention with liquid nondigestible oils are further characterized in having a relatively flat solids content profile across the temperature range of from typical room temperature to body temperature, i.e., from about 21.1° C. (70° F.) to about 37° C. (98.6° F.). The slope of the SFC profile is expressed as the change in percent solids per unit change in temperature, in °F. Typically the slope of the Solid Fat Content (SFC) profile between these temperatures is between 0 and −0.75. Generally, the greater the weight percent of $C_{20}$ or higher saturated fatty acid radicals in the solid polyol polyester, the flatter the SFC profile slope will be. For example, at the 30% $C_{20}$ or higher fatty acid level the slope will typically be between 0 and −0.5, and at 50% it will typically be between 0 and −0.3.

Determination of SFC values over a range of temperatures can be done by a method involving PNMR (Pulsed Nuclear Magnetic Resonance). Such method is well known to those skilled in the art (see *J. Amer. Oil Chem. Soc.,* Vol. 55 (1978), pp. 328-31, and A.O.C.S. Official Method Cd. 16-81, *Official Methods and Recommended Practices of The American Oil Chemists Society*, 3rd. Ed., 1987; both incorporated herein by reference).

I. Solid Polyol Fatty Acid Polyester

The solid polyol fatty acid polyester of the present invention comprises (i) a solid saturated polyol polyester, and (ii) a solid diversely esterified polyol polyester, the ratio of (i):(ii) being from about 1:19 (5% solid saturated polyol polyester) to about 4:1. The solid polyol fatty acid polyester will have a complete melt point of at least 37° C., which is the ordinary body temperature, and more preferably of at least 50° C., and most preferably of at least 60° C., and less than 500° C.

The polyols which are used in the solid polyol polyester compounds of the present invention preferably contain from about 4 to about 12, more preferably 4 to 8, most preferably 6 to 8, hydroxyl groups. Examples of preferred polyols are sugars (including monosaccharides and disaccharides and trisaccharides) and sugar alcohols, containing from 4 to 11 hydroxyl groups. The trisaccharides raffinose and maltotriose are examples of sugars which contain 11 hydroxyl groups. The preferred sugars and sugar alcohols are those which contain 4 to 8, more preferably 6 to 8, hydroxyl groups. Examples of those containing four hydroxyl groups are the monosaccharides xylose and arabinose and the sugar alcohol erythritol. Suitable five hydroxyl group-containing polyols are the mono-saccharides galactose, fructose, mannose and glucose, and the sugar alcohol xylitol. A polyol containing six hydroxyl groups is sorbitol. Examples of disaccharide polyols which can be used include maltose, lactose, and sucrose, all of which contain eight hydroxyl groups. Examples of other suitable polyols are pentaerythritol, diglycerol, triglycerol, alkyl glycosides, and polyvinyl alcohols. The preferred polyol is sucrose.

The average degree of esterification of the solid polyol fatty acid polyesters is of at least 4 ester groups, i.e., at least 4 of the hydroxyl groups of the polyol are esterified with fatty or other organic acids. Polyol esters that contain 3 or less ester groups are generally digested in (and the products of digestion are absorbed from) the intestinal tract much in the manner of ordinary triglyceride fats or oils, whereas those polyol esters which contain 4 or more ester groups are generally substantially nondigestible and consequently nonabsorbable by the human body. It is not necessary that all of the hydroxyl groups of the polyol be esterified, but it is preferable that disaccharide molecules contain no more than 3 unesterified hydroxyl groups, and more preferably no more than 2 unesterified hydroxyl groups, so that they are rendered nondigestible. Typically, substantially all (e.g., at least about 85%) of the hydroxyl groups of the polyol are esterified, preferably at least about 95% of the hydroxyl groups of the polyol are esterified. In the case of sucrose polyesters, typically from about 7 to 8 of the hydroxyl groups of the polyol are esterified.

i) Solid Saturated Polyol Polyester

The solid saturated polyol polyester of the present invention will comprise esters of essentially only, and preferably only, long chain saturated fatty acid radicals which are typically normal and contain at least 14, preferably 14 to 26, and more preferably 16 to 24, and most preferably from 20 to 24, carbon atoms. Particularly preferred are saturated fatty acid radicals of 22 carbon atoms. The long chained saturated radicals can be used in combination with each other in all proportions. The average degree of esterification of these solid saturated polyol polyesters is such that at least 4 of the hydroxyl groups of the polyol are esterified. In the case of sucrose polysaturate esters, from about 7 to 8 of the hydroxyl groups of the polyol are preferably esterified. Typically, substantially all (e.g., at least about 85%, preferably at least about 95%) of the hydroxyl groups of the polyol are esterified.

Examples of suitable long chain saturated fatty acid radicals include tetradecanoate (myristate), hexadecanoate (palmitate), octadecanoate (stearate), eicosanoate (arachidate), docosanoate (behenate), tetracosanate (lignocerate), and hexacosanoate (cerotate). Mixed fatty acid radicals from completely or substantially completely hydrogenated vegetable oils which contain substantial amounts of the desired long chain saturated fatty acids can be used as sources of fatty acid radicals in preparing the solid polyol polyesters useful in the present invention. The mixed fatty acids from such oils should preferably contain at least about 30% (more preferably at least about 50%, most preferably at least about 80%) of the desired long chain saturated fatty acids. Suitable source oils include completely or substantially completely hydrogenated soybean oil, cottonseed oil, palm oil, peanut oil, corn oil, safflower oil, sunflower oil, sesame oil, low erucic acid rapeseed oil (i.e. canola oil), and high erucic acid rapeseed oil. These oils are typically hydrogenated to an Iodine Value of about 12 or less, and preferably to an Iodine Value of about 8 or less.

Examples of solid polyol polyesters useful as hardstocks in the fat compositions of the present invention include sucrose octabehenate, sucrose octastearate, sucrose octapalmitate, sucrose heptastearate, xylitol pentastearate, galactose pentapalmitate, and the sucrose hepta- and octaesters of soybean oil and high erucic acid rapeseed oil fatty acids that have been hydrogenated to an Iodine Value of about 8 or less.

The solid saturated polyol polyester generally by itself crystallizes into well defined spherulitic particles from a molten composition at or below the onset crystallization temperature of the solid saturated polyol polyester. The onset crystallization temperature is that temperature at which a solid polyol fatty acid polyester can first begin to crystallize in the liquid polyol fatty acid polyester. That is, when dissolved in a molten composition comprising the solid saturated polyol polyester in the liquid polyol fatty acid polyester, the solid saturated polyol polyester will tend to form well defined, highly ordered, substantially sphere-shaped crystals, called spherulites, when permitted to cool and crystallize at a first crystallization temperature. The spherical shape provides optimal flowability of the crystallized solid polyol fatty acid polyester in the liquid polyol fatty acid polyester. The first crystallization temperature is within a range below the onset crystallization temperature of the specific solid saturated polyol polyester, and generally above an onset crystallization temperature of a solid diversely esterified polyol polyester.

In the absence of any solid diversely esterified polyol polyester, the solid saturated polyol polyester would normally crystallize into spherical-shaped particles called spherulites having a diameter (or maximum particle dimension) of about 3 microns or larger, usually about 3-32 microns, the size being a function of the initial concentration of the solid saturated polyol polyester in the liquid polyol fatty acid polyester.

ii) Solid Diversely Esterified Polyol Polyesters

The solid diversely esterified polyol polyester of the present invention comprises polyol polyesters which have their ester group-forming fatty acid radicals selected so that the polyol backbone does not contain all of a single type of ester group. Generally, these polyol polyesters contain two basic types of ester groups. These are (a) ester groups formed from long chain saturated fatty acid radicals, as herein above described, and (b) dissimilar ester groups formed from acid radicals which are "dissimilar" to the long chain saturated fatty acid radicals. When these "dissimilar" fatty acid and/or other organic acid radicals are esterified onto a polyol that contains or will contain long chain saturated fatty acid radicals, they will introduce diverse esterification into the resulting polyol polyester molecule, thereby altering the crystal structure as these molecules pack together during crystallization. This diverse esterification can be due to differences in length of the ester-forming acid radicals (e.g., short chain versus long chain), or other steric factors, e.g. branched chain versus straight chain, unsaturated chain versus saturated chain, aromatic chain versus aliphatic chain, etc. Polyol polyesters containing these "long chain" and "dissimilar" ester groups are therefore herein called "solid diversely esterified polyol polyesters".

The solid diversely esterified polyol polyesters tend to have "asymmetrical" or irregular molecular structures. It is believed that the asymmetrical structure of these molecules interfere with the normal packing tendency of the symmetrical solid saturated polyol polyester molecules during co-crystallization in the liquid polyol polyester. This interference blocks the usual unrestrained three dimensional growth of the solid saturated polyol polyester molecules and thus induces restrained three dimensional growth or otherwise induces growth in, at most two dimensions, e.g., the formation of relatively thin platelet-like particles.

The dissimilar ester groups are formed from acid radicals selected from long chain unsaturated fatty acid radical, short chain saturated fatty acid radical, and other dissimilar fatty acid radicals, and mixtures thereof. The preferred dissimilar acid radical is a long chain unsaturated fatty acid radical.

The long chain unsaturated fatty acid radicals are typically straight chain (i.e., normal) mono- and di-unsaturates, and contain at least about 12, preferably about 12 to about 26, more preferably about 18 to 22, and most preferably 18 carbon atoms. Examples of suitable long chain unsaturated fatty acid radicals for the solid polyol polyesters herein are lauroleate, myristoleate, palmitoleate, oleate, elaidate, erucate, linoleate, linolenate, arachidonate, eicosapentaenoate, and docosahexaenoate. For oxidative stability, the mono- and/or diunsaturated fatty acid radicals are preferred.

The short chain saturated fatty acid radicals are typically normal and contain 2 to 12, preferably 6 to 12 and most preferably 8 to 12, carbon atoms. Examples of suitable short chain saturated fatty acid radicals are acetate, butyrate, hexanoate (caproate), octanoate (caprylate), decanoate (caprate), and dodecanoate (laurate).

Other dissimilar ester-forming radicals can include fatty-fatty acid radicals having at least one hydroxyl group that is esterified with another fatty or other organic acid. Nonlimiting examples of suitable fatty-fatty acid radicals include 12-hydroxy-9-octadecenoic acid (ricinoleic acid), 12-hydroxy-octadecanoic acid, 9-hydroxy-octadecanoic acid, 9-hydroxy-10,12-octadecadienoic acid, 9-hydroxy-octadecanoic, 9,10-dihydroxyoctadecanoic acid, 12,12-dihydroxyeicosanoic acid, and 18-hydroxy-9,11,13-octadecatrienoic acid (kamolenic acid). Ricinoleic acid is a preferred hydroxy-fatty acid. Castor oil is a convenient source of ricinoleic acid. Other sources of hydroxy-fatty acids include hydrogenated castor oil, strophanthus seed oils, calendula officinalis seed oils, hydrogenated strophanthus seed oils and hydrogenated calendula officinalis seed oils, cardamine impatiens seed oils, kamala oils, mallotus discolor oils, and mallotus claoxyloides oils.

The nondigestible oil composition of the present invention can also optionally contain other solid nondigestible particles which comprise polymerized polyesters, i.e., polyol polyester polymers. Such polyol polyester polymers can be added so long as they do not significantly interfere with the formation of the solid saturated polyol polyester spherulites. Polyol polyester polymers are those formed by polymerizing a polyol polyester monomer to provide a molecule having at least two separate esterified polyol moieties linked by covalent bonds between ester groups of these different polyol moieties. For example, two sucrose octabehenate monomers could be cross-linked between fatty acids to form a polymer. Repeating units of such polyol polyester polymers can be the same or different such that the generic term "polymer" in this context includes the specific term "copolymer". The number of repeating monomer (or co-monomer) units which make up such polyol polyester polymers can range from about 2 to 20, preferably from about 2 to 12. Depending on the method of preparing them, the polyol polyester polymers are frequently oligimers containing from 2 to 4 monomeric units, i.e., are dimers, trimers, or tetramers. The most typical type of polyol polyester polymer for use herein is dimer.

When sucrose is used as the polyol of the polyester polymer, it is preferably completely esterified with fatty acid or other ester group-forming acid radicals. At least about 15%, preferably at least about 45%, more preferably at least about 75%, and most preferably at least about 90% of the hydroxyl groups of the polyol polyester polymer material should be esterified with long chain ($C_{20}$ and higher) saturated fatty acid radicals. The sucrose polyester polymers used herein can advantageously have a number average molecular weight of from about 4000 to about 60,000, preferably from about 4000 to about 36,000, more preferably from about 5000 to about 12,000.

Suitable long chain saturated fatty acid radicals for use in preparing the polyol polyester polymers (and its monomers) include those hereinbefore described for preparing the solid diversely esterified polyol polyesters. As in the case of the solid diversely esterified polyol polyesters, mixed fatty acid radicals from source oils which contain substantial amounts of the desired long chain saturated fatty acids (i.e, at least about 30%, preferably at least about 50%, more preferably at least about 80%) can be used as sources of acid radicals in preparing these polyol polyester polymers.

Suitable solid polyol polyester material which can form the solid nondigestible particles used in the fat compositions herein will generally comprise from about 0% to 99% of the polyol polyester polymer component and from 1% to about 100% of the unpolymerized polyol polyester monomer (i.e., solid saturated polyol polyester and solid diversely esterified polyol polyester) component, preferably from about 0% to about 90% of the polyol polyester polymer component and from about 10% to about 100% of the monomer component, more preferably from about 0% to 70% of the polymer component and from 30% to about 100% of the monomer component, and most preferably from about 0% to 50% of the polymer component and from 50% to about 100% of the monomer component.

Methods for preparing such polyol polyester polymers are described in U.S. Pat. No. 5,451,416, issued Sep. 19, 1995 (Johnston et. al.), the disclosure of which is incorporated herein by reference.

2. Processes for Making Solid Polyol Fatty Acid Polyesters

The solid polyol fatty acid polyesters, including both the solid saturated polyol polyester and the solid diversely esterified polyol polyester, used in the present invention can be made according to prior known methods for preparing polyesters of polyols. Since the sucrose polyesters are the preferred solid polyol polyesters herein, the invention will be exemplified primarily by these materials. One such method of preparation is by reacting the acid chlorides of the fatty acids with sucrose. In this method a mixture of the acid chloride or acid anhydrides of the fatty acids can be reacted in one step with sucrose, or the acid chlorides can be reacted sequentially with sucrose. Another preparation method is by the process of reacting methyl esters of the fatty acids with sucrose in the presence of a fatty acid soap and a basic catalyst such as potassium carbonate. See, for example, U.S. Pat. No. 3,963,699, Rizzi et al., issued Jun. 15, 1976; U.S. Pat. No. 4,518,772, Volpenhein, issued May 21, 1985; and U.S. Pat. No. 4,517,360, Volpenhein, issued May 14, 1985, and U.S. Ser. No. 07/417,490, Letton, filed Oct. 6, 1989, now abandoned, all incorporated herein by reference.

When using the methyl ester route for preparing the solid polyol polyesters herein, the fatty acid methyl esters are blended in the desired ratio and reacted with sucrose by transesterification to obtain the sucrose esters of mixed unsaturated/saturated or saturated fatty acids. In a preferred way of practicing the methyl ester process, five moles of the blended saturated/unsaturated or saturated methyl esters are reacted with sucrose in a first stage at 135° C. to obtain partial esters of sucrose. An additional nine moles of the blended esters are then added and the reaction continued at 135° C. under reduced pressure until the desired degree of esterification has been attained.

The solid saturated polyol polyester and the solid diversely esterified polyol polyester can be made separately, then mixed together to form the solid polyol fatty acid polyester portion of the nondigestible oil composition. However, in a preferred process, the two solid polyesters are made simultaneously in the same polyol esterification preparation. The preferred method of making the solid polyol fatty acid polyester is to esterify the polyol with a mixture of long chain saturated fatty acid lower alkyl (preferably methyl) esters, and dissimilar fatty acid alkyl (preferably methyl) esters selected from short chain saturated fatty acid alkyl esters, long chain unsaturated fatty acid alkyl esters, dissimilar acid alkyl esters, and mixtures thereof. When prepared in the same preparation, the esterification of the polyol hydroxy sites by the mixture of long chain saturated fatty acid radicals and dissimilar fatty acid radicals will occur substantially randomly. A minimal amount of solid saturated polyol polyester, in proportion to the solid diversely esterified polyol polyester, is needed to form at least some spherulites during the fractional crystallization step of the process of the invention. In order to ensure that a portion of the solid polyol polyesters are esterified only with long chain saturated fatty acid radicals (thereby forming solid saturated polyol polyester), it is generally required to employ about an equal proportion, and preferably proportionally more, of the long chain saturated fatty acid radicals to the dissimilar fatty acid radicals. When using sucrose, which has 8 hydroxy sites which are capable of being esterified, as the polyol, a molar ratio of long chain saturated esters to long chain unsaturated esters of 6:2 will result in about 20% on a molar basis of sucrose octasaturate and sucrose heptasaturate polyester (as the solid saturated polyol polyester), with the remaining polyesters (about 80% on a molar basis) being substantially octa- and hepta-substituted and having a mixture of long chain saturated fatty acid radicals and long chain unsaturated fatty acid radicals (as the diversely esterified polyol polyester). In an example of a preferred solid polyol polyester, a molar ratio of 6.5:1.5 of C22 saturated fatty acid ester to cottonseed oil (about 73% unsaturated) ester results in about 30 molar % solid saturated sucrose polyester and about 70 molar % solid diversely esterified sucrose polyester. Consequently, increasing the ratio of long chain saturated radicals to long chain unsaturated radicals will result in a higher proportion of the solid polyesters being converted to solid saturated polyol polyesters; conversely decreasing the ratio of long chain saturated fatty acid radicals to long chain unsaturated fatty acid radicals will tend to result in a lower proportion of the solid polyesters being converted to the solid saturated polyol polyesters.

Mixed fatty acid radicals from source oils which contain substantial amount of the desired unsaturated or saturated acids can be used as the fatty acid radicals to prepare compounds of the invention. The mixed fatty acid radicals from the oils should contain at least about 30% (preferably at least about 50%, most preferably at least about 80%) of the desired unsaturated or saturated acids. For example, rapeseed oil fatty acid radicals or soybean oil fatty acid radicals can be used instead of pure $C_{12}$-$C_{26}$ unsaturated fatty acids. Hardened (i.e., hydrogenated) high erucic rapeseed oil fatty acids can be used instead of pure $C_{20}$-$C_{26}$ saturated fatty acids. Preferably the $C_{20}$ and higher acids (or their derivatives—e.g., methyl esters) are concentrated, for example by distillation. The fatty acids from palm kernel oil or coconut oil can be used as a source of $C_8$ to $C_{12}$ acids. An example of the use of source oils to make solid polyol polyesters of the invention is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated $C_{18}$ acid radicals to $C_{20}$ and higher saturated acid radicals of about 1:1 and 28.6 weight percent of the total fatty acids in the polyester will be $C_{20}$ and $C_{22}$ fatty acids. The higher the proportions of the desired unsaturated and saturated acids in the fatty acid stocks used in making the solid polyol polyester, the more efficient the ester will be in its ability to bind liquid oils.

Examples of solid polyol polyesters of the present invention are sorbitol hexaester in which the acid ester radicals are palmitoleate and arachidate in a 1:2 molar ratio; the octaester of raffinose in which the acid ester radicals are linoleate and behenate in a 1:3 molar ratio; the heptaester of maltose wherein the esterifying acid radicals are sunflower seed oil fatty acids and lignocerate in a 3:4 molar ratio; the octaester of sucrose wherein the esterifying acid radicals are oleate and behenate in a 2:6 molar ratio; and the octaester of sucrose wherein the esterifying acid radicals are laurate, linoleate and behenate in a 1:3:4 molar ratio. A preferred material is sucrose polyester in which the degree of esterification is 7-8, and in which the fatty acid radicals are $C_{18}$ mono- and di- unsaturated and behenic, in a molar ratio of about 2:6 to about 1.5:6.5.

3. Liquid Polyol Fatty Acid Polyester

A key component of the nondigestible oil composition herein is a liquid polyol fatty acid polyester having a complete melting point below about 37° C. Suitable liquid nondigestible edible oils for use herein include liquid polyol polyesters (see Jandacek; U.S. Pat. No. 4,005,195; issued Jan. 25, 1977); liquid esters of tricarballylic acids (see Hamm; U.S. Pat. No. 4,508,746; issued Apr. 2, 1985); liquid diesters of dicarboxylic acids such as derivatives of malonic and succinic acid (see Fulcher, U.S. Pat. No. 4,582,927; issued Apr. 15, 1986); liquid triglycerides of alpha-branched chain carboxylic acids (see Whyte; U.S. Pat. No. 3,579,548; issued May 18, 1971); liquid ethers and ether esters containing the neopentyl moiety (see Minich; U.S. Pat. No. 2,962,419; issued Nov. 9, 1960); liquid fatty polyethers of polyglycerol (See Hunter et al; U.S. Pat. No. 3,932,532; issued Jan. 13, 1976); liquid alkyl glycoside fatty acid polyesters (see Meyer et al; U.S. Pat. No. 4,840,815; issued Jun. 20, 1989); liquid polyesters of two ether linked hydroxypolycarboxylic acids (e.g., citric or isocitric acid) (see Huhn et al; U.S. Pat. No. 4,888,195; issued Dec. 19, 1988); and liquid esters of epoxide-extended polyols (see White et al; U.S. Pat. No. 4,861,613; issued Aug. 29, 1989); as well as liquid polydimethyl siloxanes (e.g., Fluid Silicones available from Dow Corning). All of the foregoing patents relating to the liquid nondigestible oil component are incorporated herein by reference.

Preferred liquid nondigestible oils are the liquid polyol polyesters that comprise liquid sugar polyesters, liquid sugar alcohol polyesters, and mixtures thereof. The preferred sugars and sugar alcohols for preparing these liquid polyol polyesters include erythritol, xylitol, sorbitol, and glucose, with sucrose being especially preferred. The sugar or sugar alcohol starting materials for these liquid polyol polyesters are preferably esterified with fatty acids containing from 8 to 22 carbon atoms, and most preferably from 8 to 18 carbon atoms. Suitable naturally occurring sources of such fatty acids include corn oil fatty acids, cottonseed oil fatty acids, peanut oil fatty acids, soybean oil fatty acids, canola oil fatty acids (i.e. fatty acids derived from low erucic acid rapeseed oil), sunflower seed oil fatty acids, sesame seed oil fatty acids, safflower oil fatty acids, fractionated palm oil fatty acids, palm kernel oil fatty acids, coconut oil fatty acids, tallow fatty acids and lard fatty acids.

The nondigestible polyol polyesters that are liquid are those which have minimal or no solids at body temperatures (i.e., 98.6° F., 37° C.). These liquid polyol polyesters typically contain ester groups having a high proportion of $C_{12}$ or lower fatty acid radicals or else a high proportion of $C_{18}$ or higher unsaturated fatty acid radicals. In the case of those liquid polyol polyesters having high proportions of unsaturated $C_{18}$ or higher fatty acid radicals, at least about half of the fatty acids incorporated into the polyester molecule are typically unsaturated. Preferred unsaturated fatty acids in such liquid polyol polyesters are oleic acid, linoleic acid, and mixtures thereof.

The following are nonlimiting examples of specific liquid polyol polyesters suitable for use in the present invention: sucrose tetraoleate, sucrose pentaoleate, sucrose hexaoleate, sucrose heptaoleate, sucrose octaoleate, sucrose hepta- and octaesters of unsaturated soybean oil fatty acids, canola oil fatty acids, cottonseed oil fatty acids, corn oil fatty acids, peanut oil fatty acids, palm kernel oil fatty acids, or coconut oil fatty acids, glucose tetraoleate, the glucose tetraesters of coconut oil or unsaturated soybean oil fatty acids, the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

The liquid polyol polyesters suitable for use in the compositions herein can be prepared by a variety of methods known to those skilled in the art. These methods include: transesterification of the polyol (i.e. sugar or sugar alcohol) with methyl, ethyl or glycerol esters containing the desired acid radicals using a variety of catalysts; acylation of the polyol with an acid chloride; acylation of the polyol with an acid anhydride; and acylation of the polyol with the desired acid, per se. (See, for example, U.S. Pat. Nos. 2,831,854, 3,600,186, 3,963,699, 4,517,360 and 4,518,772, all of which are incorporated by reference. These patents all disclose suitable methods for preparing polyol polyesters.)

4. Other Shortening Ingredients

So long as they do not interfere with the formation of the flowable nondigestible oil, the flowable nondigestible oil compositions may also comprise other shortening ingredients. Various additives can be used herein provided they are edible and aesthetically desirable and do not have any detrimental effects on the shortenings. These additives include edible, digestible oils and hardstock, fat-soluble vitamins, flavorings and seasonings, emulsifiers, anti-spattering agents, chelating agents, anti-sticking agents, anti-oxidants, anti-foaming agents (for frying applications) or the like.

5. Formation of Stiffened Nondigestible Oil

Ordinarily, and when not practicing the process of the present invention, the solid polyol fatty acid polyester component of the nondigestible oil composition described herein is capable of crystallizing from a molten liquid form to a stiffened nonflowable oil form when the composition is rapidly cooled from the molten temperature to the second crystallization temperature, or less (for example, to the body temperature of about 37° C.) under substantially quiescent conditions. This stiffened nonflowable nondigestible oil comprises the liquid nondigestible oil portion retained substantially completely within the crystalline matrix of crystallized solid polyol fatty acid polyester, thereby providing the desired passive oil loss control of the nondigestible oil. The composition and method of making of the food composition should be selected to provide the sufficiently rapid cooling of the nondigestible oil from a molten temperature to a lower temperature substantially in the absence of shearing of the food composition, such that the solid polyol fatty acid polyester has crystallized into the desired crystalline form which provides the desired passive oil loss control. Generally, this cooling rate from the onset crystallization temperature of the highest melting solid saturated polyol polyester to the lowest selected second crystallization temperature is greater than about 0.5° C./min, more preferably greater than about 2.5° C./min, and most preferably greater than 25° C./min. In the case of a polyol polyester polymer, which can form the desired crystal structure for passive oil loss control at much slower cooling rates, a cooling rate of greater than about 0.03° C./min. under the quiescent conditions is generally sufficient to form the desired crystal structure.

When a nondigestible oil composition comprising solid, polyol fatty acid polyester containing both the solid saturated polyol polyester and solid diversely esterified polyol polyester begin to co-crystallize in the liquid polyol polyester, the co-crystals initially appear as discrete, unaggregated entities, suspended in the liquid polyol fatty acid polyester. Under quiescent cooling conditions, such as when the molten nondigestible oil has been processed into food products via baking or frying, these discrete unaggregated entities can grow as crystallization continues, and begin to cluster together to form small aggregates of at least 3 microns, dispersed in the liquid nondigestible oil. These small aggregate clusters of particles can develop in a variety of forms and shapes, including spherical, platelet-like, filament-like or rod-like, or combinations of these various shapes, but are typically spherical or platelet-like. Thinner aggregate particles, referred to as platelets, are preferred from the standpoint of providing more efficient passive oil loss control of the liquid polyol polyester component of the nondigestible oil compositions herein. These platelet particles preferably have a thickness of about 0.1 micron or less, more preferably about 0.05 micron or less. As the crystallization continues, the platelets continue to grow and to cluster together to form a larger aggregate particle that is porous in character and thus capable of entrapping significant amounts of the liquid polyol polyester. It is believed that this porous structure and its concomitant ability to entrap large amounts of liquid polyol polyester is why these larger aggregated, platelet-like particles can provide very effective and efficient passive oil loss control, and results in a stiffened, nonflowable nondigestible oil.

B. Process for Making a Flowable Nondigestible Oil Composition

The present invention provides a process for making a flowable nondigestible oil wherein the solid polyol fatty acid polyester comprises a solid saturated polyol polyester capable of forming spherulites. The process comprises the steps of melting completely a nondigestible oil composition comprising the solid polyol fatty acid polyester and the liquid polyol fatty acid polyester, crystallizing a portion of the solid saturated polyol polyester into spherulites, thereby forming a partially crystallized polyol polyester composition, and further crystallizing a remaining portion of the solid polyol fatty acid polyester, thereby forming the flowable nondigestible oil composition.

Without the invention being bound by any theory of crystallization described herein, it is understood that crystallization of the solid diversely esterified polyol polyester and the solid saturated polyol polyester occurs kinetically. As with any kinetic reaction, a dynamic equilibrium can be achieved wherein the reaction may appear to have halted. Then, by changing the conditions, the reaction can be made to proceed forward, or even to reverse. In the same way, the solid polyol fatty acid polyester can crystallize under a condition until a dynamic equilibrium is achieved. The dynamic equilibrium can exist wherein a portion of a solid polyol fatty acid polyester is still dissolved in the liquid polyol fatty acid polyester while the preponderance has been crystallized.

The rate at which a solid polyol fatty acid polyester will crystallize depends upon several factors, such as, the molecular composition of the solid polyol fatty acid polyester, the concentration of the solid polyol fatty acid polyester, the proportion of solid polyol fatty acid polyester already crystallized to that remaining dissolved in the liquid polyol fatty acid polyester, and the temperature differential between the onset crystallization temperature of the solid polyol fatty acid polyester and the temperature of crystallization. At the onset of crystallization at the first crystallization temperature, a solid saturated polyol polyester will initially crystallize at a high crystallization rate into well-defined spherulitic particles. This crystallization rate slows with time, eventually (and ideally) to a rate of zero. Then, when the solution is further cooled to a lower temperature the equilibrium is shifted such that additional solid polyol fatty acid polyester can crystallize from the liquid polyol polyester. While the proportion of solid polyol fatty acid polyester which will crystallize with an incremental reduction in temperature is generally low, it is believed that additional crystallizing solid saturated polyol polyester will tend to crystallize onto other spherulites, causing these to grow larger in size, or to form additional new crystal nuclei, due to the highly ordered nature of the saturated polyester. The solid diversely esterified polyol polyester which begins to crystallize at the second crystallization temperature will tend to crystallize as discrete, unaggregated entities suspended in the liquid polyol fatty acid polyester or onto other aggregate particles, or more likely, as discrete crystals onto the surface of a spherulite particle. In the presence of applied shear, the discrete unaggregated entities may begin to cluster together to form small aggregates, typically up to several microns in size. However, these aggregate particles do not generally continue to cluster into a large matrix of crystal aggregate in the presence of shearing, thereby promoting the flowability of the nondigestible oil.

The present process of making a flowable polyol polyester requires at least about 10 minutes, and generally no more than about 5 hours, preferably at least about 20 minutes and no more than about 2 hours, and more preferably at least about 30, minutes and no more than about 60 minutes. The nondigestible oil composition used in accordance with the present invention which is simply directly cooled from a molten temperature to an ambient temperature substantially in a quiescent condition (that is, without shearing) within these same time periods, would develop into a stiffened, nonflowable composition comprising crystalline solid polyol fatty acid polyester, having a Consistency of more than about 600 P.sec$^{(n-1)}$ at ambient temperature.

I. Fractional Crystallization of the Solid Saturated Polyol Polyester

The step which characterizes the process of the present invention comprises crystallizing a portion of the solid saturated polyol polyester into spherulites, thereby fractionally crystallizing the solid saturated polyol polyester from the solid polyol fatty acid polyester blend. This step can comprise the sub-steps of reducing the temperature of the melted nondigestible oil composition to a first crystallization temperature less than the onset crystallization temperature of the solid saturated polyol polyester, and holding the nondigestible oil composition at the first crystallization temperature for a time sufficient to crystallize the portion of the solid saturated polyol polyester into crystallized spherulites, thereby forming a partially crystallized polyol polyester composition. Preferably, the first crystallization temperature is at least 1° C., more preferably at least 2° C., and most preferably at least 3° C., below the onset crystallization temperature of the solid saturated polyol polyester. Furthermore, the first crystallization temperature should be selected such that crystallization of solid diversely esterified polyol polyester is avoided, since such could disrupt the formation of the flow-efficient spherulites. This step, and thus this process, generally requires that the onset crystallization temperature of the solid saturated polyol polyester be greater than the onset crystallization temperature of the solid diversely esterified polyol polyester in the nondigestible oil. Preferably the first crystallization temperature is at least about 1° C., more preferably at least 2° C., and most preferably at least 3° C., higher than the onset crystallization temperature of the solid diversely esterified polyol polyester.

During the first crystallization step, the application of shear to the nondigestible oil composition is optional. In a preferred embodiment, sufficient shear to the composition is applied uniformly to ensure the composition is homogenous, to increase the rate of crystallization of the solid saturate polyol polyester. The amount of shear that is preferably employed is about 50 sec$^{-1}$. If the high rates of shear (greater than about 100 sec$^{-1}$) are applied during the first crystallization step, the general tendency will be for smaller and more numerous spherulties to form. Under extremely high rates of shear, spherulites may be caused to crack and break into two or more pieces, each piece of which then grows as additional solid saturated polyol polyester is crystallized thereon.

The amount of time required to complete the first crystallization step is generally at least about 5 minutes, preferably at least about 10 minutes, and most preferably at least about 20 minutes. In general, it will not be necessary to continue the process for longer than 30 minutes. The crystallization time can be minimized by selecting a first crystallization temperature that is sufficiently lower than the onset crystallization temperature of the solid saturated polyol polyester to ensure a optimum driving force for crystallization.

Although the first crystallization temperature can be varied in the preferred ranges described above, it is generally preferred to maintain a constant temperature, or to reduce the temperature slowly through a preferred range in order to encourage the fractional crystallization to proceed most rapidly on account of the temperature differential between the onset crystallization temperature and the first crystallization temperature.

When the solid saturated polyol polyester comprises two or more distinct polyester components which have different onset crystallization temperatures, then the steps of fractional crystallizing can be conducted at successively lower first crystallization temperatures corresponding to the individual solid saturated polyol polyester components, or at a single first crystallization temperature which is below the onset crystallization temperature of each of the two or more components.

Figure 1B:
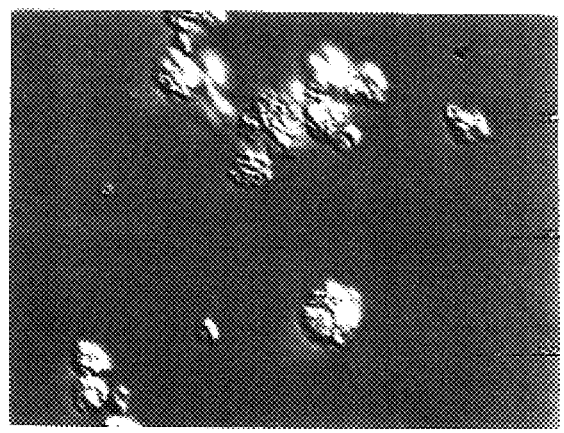
Figure 1C:
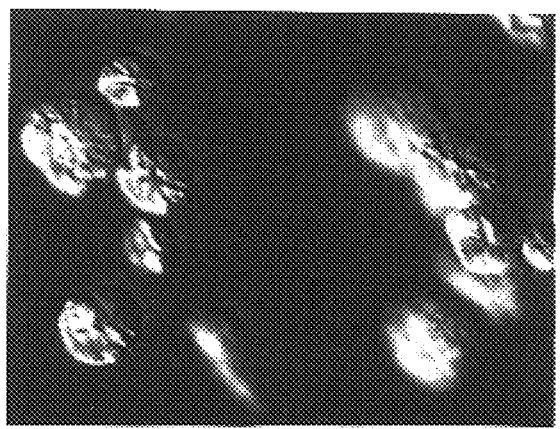
Figure 1D:
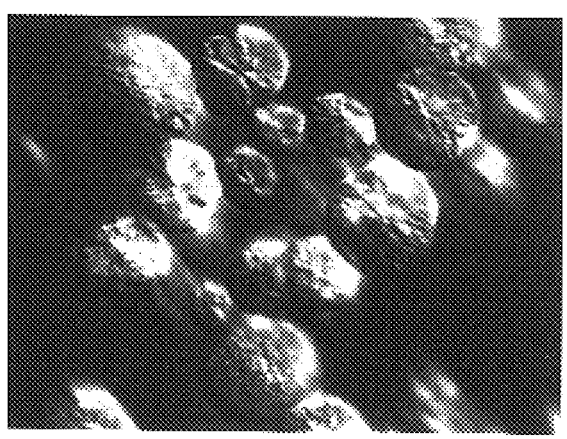
Figure 2:
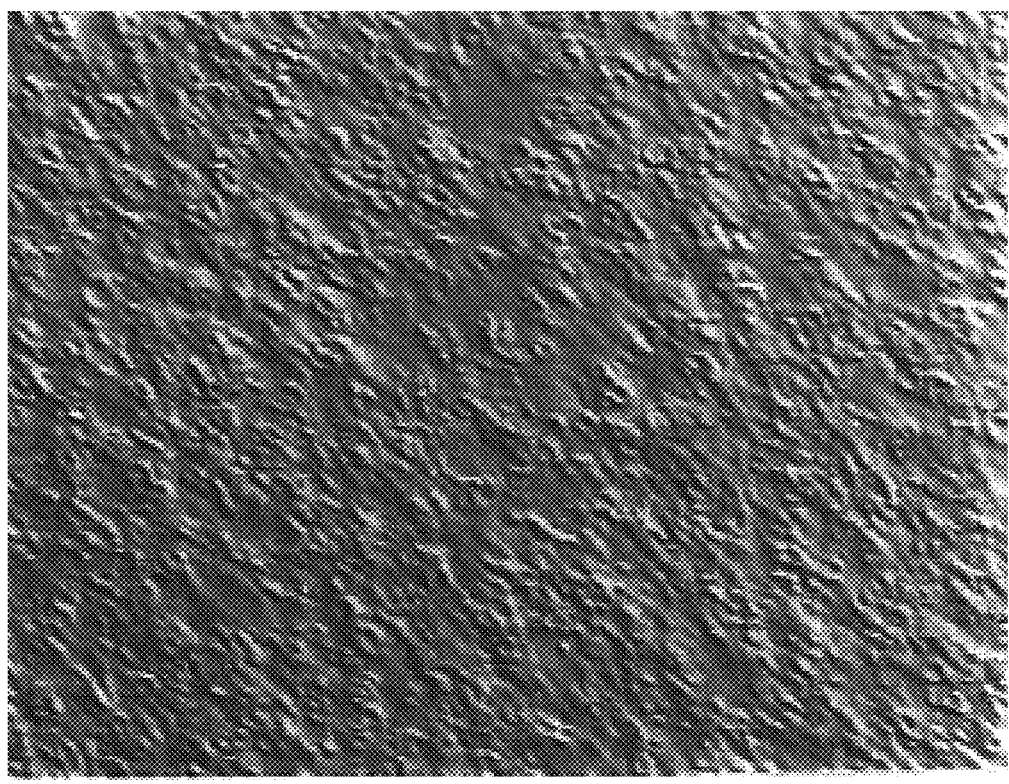
FIG. 2 is a photomicrograph (magnification 1000x) depicting a rapidly cooled, co-crystallized blend of a solid saturated sucrose polyester and a solid diversely esterified sucrose polyester which were made using a mixture of lauric and behenic fatty acids in a molar ratio of 1:7, the blend being dispersed in a liquid sucrose polyester at a total solids level of 3% by weight, where the ratio of solid saturated sucrose polyester to solid diversely esterified sucrose polyester is 6:4. The nondigestible oil composition is nonflowable and was not made in accordance with the present invention.
Figure 3:
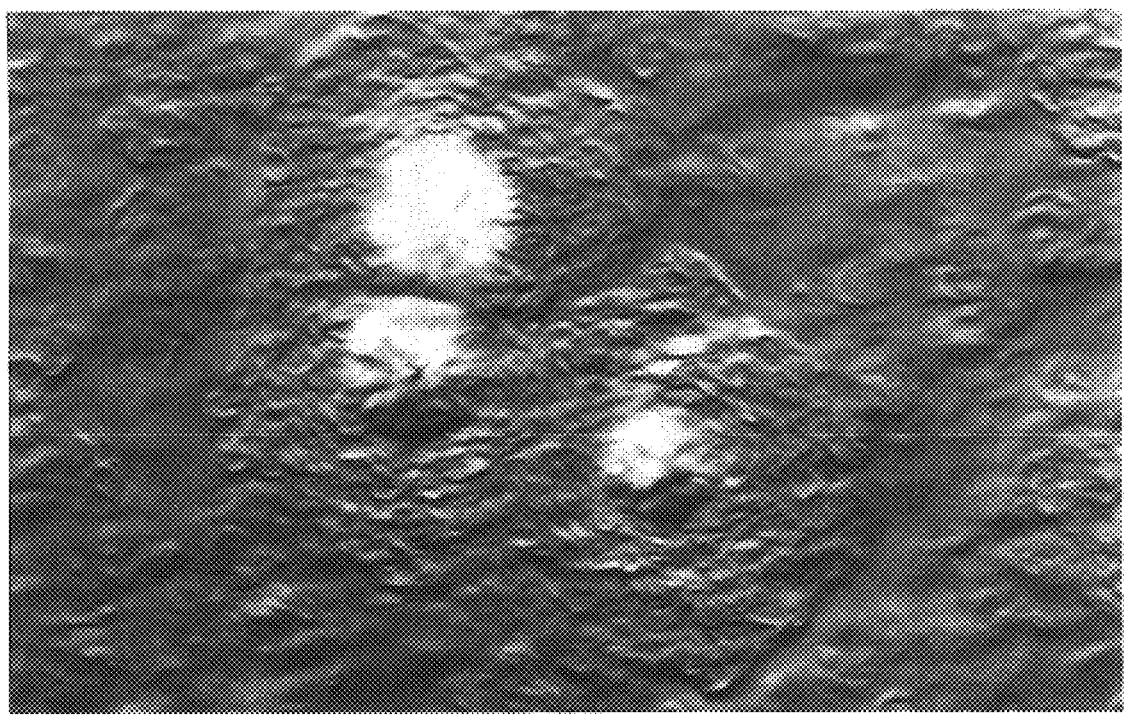
FIG. 3 is a photomicrograph (magnification 1000x) depicting flowable oil composition made in accordance with the present invention containing spherulites made with solid saturated sucrose polyester having crystallized upon the surfaces thereof solid diversely esterified polyol polyester, which were made using a mixture of behenic and linoleic fatty acids in a molar ratio of 1.5:6.5, the blend being dispersed in a liquid sucrose polyester at a total solids level of 6% by weight. The nondigestible oil composition is flowable and have a Consistency of less than 600 P.sec$^{(n-1)}$.

A solid saturated polyol polyester, in the absence of solid diversely esterified polyol polyester, will crystallize in the liquid polyol fatty acid polyester to normally form spherulites having a diameter of about 3 microns or larger, and typically in the range of from about 3 to about 32 microns, depending on the level of solid saturated polyol polyester present and the rate of shearing (if any) during crystallization. The solid saturated polyol polyester tends to form such spherulites due to the symmetrical nature of the molecules which enable them to pack together and grow in an unrestrained, three-dimensional fashion as large spherulites. FIGS. 1a, 1b, 1c and 1d are photomicrographs showing a typical solid saturated sucrose polyester made with esters derived from soybean oil, hydrogenated to an Iodine Value of about 8 or less, crystallized in a liquid nondigestible oil made with esters derived from cottonseed oil, at levels of 1%, 3%, 6% and 9%, by weight, respectively.

In the molten state, the nondigestible oil compositions are generally transparent and clear. It will be observed that as solid polyol fatty acid polyester begins to crystallize (at and below the onset crystallization temperature of the solid polyol fatty acid polyesters), the liquid polyol polyester begins to become turbid and clouded. The "onset crystallization temperature" for a solid polyol fatty acid polyester can be determined by the method described below in the Analytical section.

2. Crystallization of the Solid Diversely Esterified Polyol Polyester

The next step of the process comprises crystallizing a remaining portion of the solid polyol fatty acid polyester. This step can comprise the steps of reducing the temperature of the partially crystallized polyol polyester composition to a second crystallization temperature, and holding the polyol polyester composition at the second temperature for a time sufficient to crystallize a remaining portion of the solid polyol fatty acid polyester, which can be a remaining portion of the solid saturated polyol polyester, a portion of the solid diversely esterified polyol polyester, or both.

In a preferred process, the next step of crystallizing further comprises applying shear energy during the step of crystallizing the remaining portion of solid polyol fatty acid polyester at the second crystallization temperature.

Generally, the onset crystallization temperature of the solid saturated polyol polyester will be above the onset crystallization temperature of the solid diversely esterified polyol polyester. Preferably, the difference between the onset crystallization temperatures of the solid saturated polyol polyester and solid diversely esterified polyol polyester is sufficient to permit rapid crystallization of the solid saturated polyol polyester into the large spherulites, though avoiding co-crystallizing of the solid diversely esterified polyol polyester with the solid saturated polyol polyester. Typically the difference in onset crystallization temperatures is more than 3° C., preferably more than 5° C., and most preferably more than about 10° C.

To form a flowable nondigestible oil composition with the most preferred flowability for storage and use at ambient temperatures, it is preferable to process the composition such that the crystallization of the solid diversely esterified polyol polyester, after crystallization of the solid saturated polyol polyester into large spherulites, will substantially avoid forming the large aggregate particles clustered together, which result in a less flowable nondigestible oil.

One method of forming the flowable nondigestible oil involves crystallizing the portion of the solid diversely esterified polyol polyester onto the surfaces of the spherulites (formed from solid saturated polyol polyesters). The crystallization of the solid diversely esterified polyol polyester onto the surfaces of the crystallized spherulites results in an aggregated spherulite, which comprises a spherulite particle core surrounded or coated substantially with aggregate particles of the solid diversely esterified polyol polyester. The structure of this aggregate spherulite can be described as similar to cotton balls with a solid center core. By applying shear energy to the composition during crystallization, the potential is reduced for adjacent aggregated spherulitic particles to become clustered together, which tends to result in a more flowable nondigestible oil. Also, the dimensions and the porosity of the aggregate formed on the surface of the spherulite may be reduced or compressed. The size of the small aggregated spherulites (comprising a spherulite core with aggregate solid diversely esterified polyol polyester crystallized to its surface) as described herein are generally about 1 micron to about 50 microns. Preferably they are from about 1 micron to about 30 microns, and more preferably from about 1 micron to about 10 microns.

In a process in accordance with this method of forming the flowable nondigestible oil, it is generally preferred to reduce the second crystallization temperature slowly through the temperature range where the solid diversely esterified polyol polyester crystallizes, in order to likewise slow the rate of crystal formation of the solid diversely esterified polyol polyester. This slow rate of temperature reduction is believed to promote formation of solid diversely esterified polyol polyester crystals on the surface of the spherulites, as opposed to formation of the aggregates or unaggregated crystals of solid diversely esterified polyol polyester in the liquid polyol polyester. The second crystallization temperature can be maintained constant, or varied, within the second crystallization temperature range. In order to maximize the crystallization of solid diversely esterified polyol polyester onto the surface of spherulites, which in turn tends to result in a more flowable nondigestible oil having a lower Consistency, the rate of cooling is typically no greater than 5° C./min., preferably no greater than 2° C./min., and at least 0.1° C./min. More preferably the cooling rate is about 0.5-0.7° C./min. Preferably the rate of cooling is accompanied by moderate agitation which ensures that the composition is well mixed in the crystallization vessel, and promotes transport of solid diversely esterified polyol polyester to the surface of the spherulite for crystallization.

An alternative method of forming the flowable nondigestible oil is to prevent any free small aggregate particles and/or platelets formed during the crystallization of solid diversely esterified polyol polyester, from becoming clustered together and forming a less flowable nondigestible oil. These aggregates are formed in the liquid polyol polyester, and can be formed along with crystallization of solid diversely esterified polyol polyester onto spherulites. Crystallization in the liquid polyol polyester generally results when the cooling through the second crystallization temperature occurs more rapidly. By applying mechanical shear to the composition during the crystallization, the small aggregate particles and platelets are prevented from clustering together into larger aggregate particles. The shear energy also can result in tearing or breaking apart of larger aggregate particles into the smaller aggregate particles. In addition, the shear energy is theorized to compress the crystal structures of the smaller aggregate particles such that their dimensions and porosity are reduced. In other words, shear energy can be applied to prevent clustering of the smaller aggregate particles of solid polyol polyester into larger aggregate particles, and to reduce the particle dimensions and porosity of the small aggregate particles into smaller compressed aggregate particles. In a process in accordance with this method of forming the flowable nondigestible oil, it is generally preferred to reduce the second crystallization temperature rapidly through the temperature range where the solid diversely esterified polyol polyester crystallizes, which results in a rapid rate of crystal formation of the solid diversely esterified polyol polyester. The cooling rate is typically more than about 3° C./min., and can be up to about 80° C./min. Preferably the rate of cooling is accompanied by moderate to high shear agitation.

In a preferred process, the composition is reduced through or to the second crystallization temperature at a very high rate. A scraped wall heat exchanger is a preferred apparatus for rapidly reducing the temperature of the composition, at rates typically of about 8-80° C./min. This rapid rate of temperature reduction promotes formation of solid diversely esterified polyol polyester crystals into aggregates or unaggregated crystals of solid diversely esterified polyol polyester in the liquid polyol polyester, as opposed to formation of the crystals on the surface of the spherulites. This rapid rate of temperature cooling results in a more rapid process for forming the flowable nondigestible oil. Preferably, the rapid cooling of the composition is accompanied with very high shearing to prevent a matrix of large aggregates from forming. The scraped wall heat exchanger is capable of delivering such high shear while cooling the composition.

Preferably a tempering step as described below is used following rapid cooling crystallization with high shearing, as described above.

The size of the small aggregate particles of the present invention as described herein above are generally about 1 micron to about 30 microns. Preferably these aggregate esterified polyol polyester are from about 1 micron in maximum dimension to about 10 microns.

3. Tempering

The process of the present invention can preferably include a tempering of the flowable nondigestible oil. The tempering step comprises reducing the temperature of the partially crystallized polyol polyester composition to a second crystallizing temperature (here, a tempering temperature) that is less than the intended minimum handling and storage temperature of the flowable nondigestible oil, and holding the composition at the tempering temperature for a time sufficient for the solid polyol polyester to substantially complete crystallizing. The tempering temperature is preferably at least 5° C., more preferably at least 10° C., below the intended ambient handling/storage temperature of the flowable nondigestible oil. Typically, the tempering temperature is from about 5° C. to about 25° C. preferably about 5° C. to about 15° C.

In order to prevent the aggregation of crystallized particles during the tempering step, shear mixing should be applied to the polyol polyester composition in an amount and for a time sufficient to form the flowable composition. In general the tempering step will take from about 2 minutes to about 1 hour, more preferably about 5 minutes to about 20 minutes. The amount of shearing that is typically provided is about 1-50 sec$^{-1}$, more preferably about 25 sec$^{-1}$.

The tempering step preferably includes the step of rapidly crystallizing the composition using a scraped surface heat exchanger to minimize the time needed to process the temperature rapidly to the tempering temperature. In a preferred process, a significant portion of the solid diversely esterified polyol polyester is crystallized by cooling the composition through the second crystallization temperature at a slow rate, to promote crystallization of the crystals on the surfaces of the spherulites; then the temperature of the composition is cooled rapidly to a tempering temperature and held for a time sufficient to crystallize a substantially all of the remaining portion of solid diversely esterified polyol polyester.

Following the tempering step, the flowable polyol polyester composition is preferably raised in temperature to the ambient handling/storage temperature.

4. Diluent Addition

The process of the present invention can also preferably include a step of adding a diluent liquid to the crystallized composition in order to form, or to ensure the stability of, the flowable nondigestible oil. The principle of adding a diluent liquid is to increase incrementally the solubility of the solid polyol polyester into the liquid polyol polyester, thereby promoting a more flowable composition. Preferably the diluent liquid is added after the second crystallization temperature has been reduced to the ambient storage temperature, even more preferably after any tempering step. The addition of the diluent can stop the driving force for solid polyol polyester in the liquid polyol polyester to crystallize out of solution, and can even result in some amount of re-solubilizing of crystallized solid polyol polyester back into the liquid phase. The diluent is added in an amount, relative to the amount of the processed nondigestible oil, generally at about 10:1 to about 0.01:1, preferably about 2:1 to about 0.01:1, more preferably about 1:1 to about 0.05:1, and most preferably about 0.5:1 to about 0.1:1. The temperature of the diluent liquid at which it is added to the flowable nondigestible oil is from about 5° C. to about 50° C., more preferably about 10° C. to about 25° C. The temperature of the diluent liquid will depend upon the amount of diluent liquid used, the preferred storage temperature of the flowable nondigestible oil, and other factors that will be understood by one skilled in the art. A preferred diluent is the liquid polyol polyester. Other diluents can be other edible oils, preferably nondigestible oils, which are miscible with the liquid polyol polyester of the flowable nondigestible composition, and are generally lipophilic.

5. Processing Systems

The flowable nondigestible oil composition of the present invention may be processed by techniques commonly employed to crystallize fats. For example, in order to rapidly reduce the temperature of a molten oil composition, the composition can be passed through a conventional scraped surface heat exchanger. The fluid nondigestible oil composition can be maintained at a selected process temperature, such as during the first crystallization step, using conventional means such as in a tank with agitation or recirculation means, preferably with temperature controls using internal or external heat exchanger means. To shear a liquid as described herein, a standard paddle agitator, as an example, can be used, provided that the agitation system is able to shear the entire contents of the tank.

The process according to present invention can further comprise the step of periodically applying shear in an amount sufficient to maintain the Consistency of a flowable nondigestible oil in a temperature of 20-40° C. of less than about 600 P.sec$^{(n-1)}$, preferably less than about 400 P.sec$^{(n-1)}$. If the flowable nondigestible oil composition is permitted to set without any circulation or stirring for an extended period of time, it is possible that minor temperature fluctuations could result in an incremental crystallization of remaining solid polyol polyester in the liquid polyol polyester, which could result in a thickening and stiffening of the composition. Application of additional shear, therefore, would serve to break up any larger aggregate particles that may have formed from the clustering of small aggregate particles, thereby reducing the Consistency of the composition.

C. Temperature Sensitive Food Additives

The flowable nondigestible oil composition can further comprise temperature-sensitive food additives, including fat-soluble and other vitamins, flavorings, and seasonings. The food additives can be added either as a particulate or as a liquid. When adding as a particulate, the particulate food additive can be added to the final flowable nondigestible oil, or added during the crystallization of the compositions at a step where the temperature does not adversely effect the efficacy of the additive.

The present flowable nondigestible oil compositions can also be fortified with vitamins and minerals, particularly the fat-soluble vitamins. The fat-soluble vitamins include vitamin A, vitamin D, vitamin K, and vitamin E. (See U.S. Pat. No. 4,034,083 (Mattson) issued Jul. 5, 1977, incorporated by reference herein.)

D. Uses of the Nondigestible Oil Compositions

The nondigestible oils, which can be processed into the flowable nondigestible oils of the present invention, can be used in frying applications such as the preparation of French fried potatoes, potato chips, corn chips, tortilla chips, chicken, fish, and battered and fried foods (e.g. shrimp tempura). Preferably, the compositions can be used as shortenings, cooking oils, frying oils, salad oils, and popcorn oils. The compositions may also be used in cooking sprays, margarines and spreads. The individual composition components may be mixed before preparing foods or they can be added separately to the foods.

The nondigestible oils can also be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, granola bars, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, and baked farinaceous snack foods, and other baked salted snacks.

The herein can also be used as a component of the fat portion of many other foods such as ice cream, frozen desserts, cheese, meats, chocolate confections, salad dressings, mayonnaise, margarine, spreads, sour cream, yogurt, coffee creamer, extruded snacks, roasted nuts and beverages, such as milk shakes.

The compositions of the present invention can be used to substitute from about 10% to 100% of the fat/oil in foods. When substituting the present compositions for fat in foods which contain fat and non-fat ingredients (e.g., starches, sugar, non-fat milk solids, etc.) the solid polyol polyesters are included to control passive oil loss of the nondigestible oil when said foods are ingested.

The compositions herein can be used in combination with other nondigestible fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the materials herein are medium chain triglycerides, triglycerides made with combinations of medium and long chain fatty acids (like the ones described in European Application 0322027 (Seiden), published Jun. 28, 1989, incorporated herein by reference), highly esterified polyglycerol esters, acetin fats, plant sterol esters, polyoxyethylene esters, jojoba esters, mono/diglycerides of fatty acids, and mono/diglycerides of short-chain dibasic acids.

The compositions are particularly useful in combination with particular classes of food and beverage ingredients. For example, an extra calorie reduction benefit is achieved when the present flowable shortenings are used with noncaloric or reduced calorie sweeteners alone or in combination with bulking agents. Noncaloric or reduced calorie sweeteners include, but are not limited to, aspartame, saccharin, alitame, thaumatin, dihydrochalcones, acesulfame and cyclamates.

Bulking or bodying agents are useful in combination with the nondigestible oil compositions herein in many food compositions. The bulking agents can be nondigestible carbohydrates, for example, polydextrose and cellulose or cellulose derivatives, such as carboxymethylcellulose, carboxyethylcellulose, hydroxypropyl methylcellulose, hydroxypropylcellulose, methyl cellulose and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

Similarly, food and beverage compositions can be made that combine the present nondigestible oil compositions with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and manmade fibers (for example, by bacterial synthesis). Commercial fibers such as purified plant cellulose, or cellulose flour, can also be used. Naturally occurring fibers, such as psyllium, and fibers from whole citrus peel, citrus albedo, sugar beets, citrus pulp and vesicle solids, apples, apricots, and watermelon rinds.

These dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Of course, judgment must be exercised to make use of the present compositions and combinations thereof with other food ingredients. For example, a combination of sweetener and present flowable compositions would not be used where the specific benefits of the two are not desired. The composition and flowable composition/ingredient combinations are used where appropriate, and in appropriate amounts.

Many benefits are obtained from the use of the these nondigestible oil composition in food and beverage compositions, either when used alone or in combination with edible oils and/or other ingredients discussed above. A primary benefit is the calorie reduction achieved when nondigestible oil compositions are used as a total or partial fat replacement. This calorie reduction can be increased by using combinations of the present nondigestible oil compositions with reduced calorie sweeteners, bulking agents, or other nondigestible fats and oils. Another benefit which follows from this use is a decrease in the total amount of digestible fats in the diet. Furthermore, a significant reduction in saturated fat consumption can be achieved by substituting the present nondigestible oil compositions for saturated fats in the diet. Foods or beverages made with the nondigestible solid fat materials instead of animal-derived triglyceride fats will also contain less cholesterol, and the ingestion of these foods can lead to reduced serum cholesterol and thus reduced risk of heart disease. Also, compositions made with these fat materials have acceptable organoleptic properties, particularly lack of waxiness.

Dietary foods can be made with the nondigestible oil compositions, to meet special dietary needs, for example, of persons who are obese, diabetic, or hypercholesterolemic. The present compositions can be a major part of a low-fat, low-calorie, low-cholesterol diet, and they can be used alone or in combination with drug therapy or other therapy. Combinations of food or beverage products made with the present nondigestible oil compositions can be used as part of a total dietary management regimen, based on one or more of these products, containing the fat materials alone or in combination with one or more of the above-mentioned ingredients, to provide one or more of the above-mentioned benefits.

This discussion of the present nondigestible oil composition uses, combinations, and benefits is not intended to be limiting or all-inclusive. It is contemplated that other similar uses and benefits can be found that will fall within the spirit and scope of this invention.

In addition to food compositions, the flowable or nonflowable nondigestible oil compositions of the present invention can be used in formulating lubricants, skin creams, pharmaceuticals, cosmetics, and the like.

The invention will be illustrated by the examples which follow the analytical methods.

E. Processing of Flowable Nondigestible Oil into Food and Beverage Products

The present flowable compositions are useful in the preparation of a wide variety of food and beverage products. Because of the processing steps in the present invention, the resulting flowable nondigestible oil composition, if consumed in its form directly or in foods containing the flowable nondigestible oil, may have relatively poor passive oil loss control. Consequently, it is important first to completely melt the flowable nondigestible oil to a completely molten nondigestible oil, such that the crystallized solid polyol fatty acid polyester is substantially completely melted. Preferably, the flowable nondigestible oil is melted up to a temperature of about 10° C. or more above the complete melt point of the solid polyol fatty acid polyester. The molten nondigestible oil can then be processed into food and beverage compositions in a manner that provides sufficiently rapid cooling of the nondigestible oil in a substantially quiescent state in the food product (that is, without applying shear during the crystallization) to yield a solid polyol polyester crystalline structure that provides good passive oil loss control.

Alternatively, the flowable nondigestible oil can be applied into the food-making process directly, so long as the processing results in a substantially complete melting of the solid polyol fatty acid polyester, and subsequent rapid cooling of the molten nondigestible oil to provide the good passive oil loss control. An example of such a process is spraying of the flowable nondigestible oil onto the surface of a snack food just after frying or baking. Because the snack food is still hot, the flowable nondigestible oil will be substantially completely melted, including the solid polyol fatty acid polyester thereof, and will subsequently crystallize into a form displaying passive oil loss control as the snack food cools rapidly. Another example of such a process is baking of crackers in which a flowable nondigestible oil is mixed into the cracker dough and then heated in an oven to temperatures at least 10° C. above the complete melting point of the solid polyol fatty acid polyester.

When the flowable nondigestible oil composition comprises a temperature sensitive food additive, such as a vitamin, then it is important that the time during which the nondigestible oil composition is in its re-melted state should be kept to a minimum to avoid loss of efficacy of the vitamin.

F. Analytical Methods (a). Solid Fat Content

Before determining Solid Fat Content (SFC values, a sample of the flowable composition or mixture of nondigestible liquid/solid is heated to a temperature of 140° F. (60° C.) or higher for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; and at 32° F. (0° C.) for 15 minutes. After tempering, the SFC values of the sample at temperatures of 50° F. (10° C.), 70° F. (21.1° C.), 80° F. (26.7° C.), 92° F. (33.3° C.) and 98.6° F. (37° C.), can be determined by pulsed nuclear magnetic resonance (PNMR) after equilibration for 30 minutes at each temperature. The method for determining SFC values by PNMR is described in Madison and Hill, *J. Amer. Oil Chem. Soc.,* Vol. 55 (1978), pp. 328-31 (herein incorporated by reference). Measurement of SFC by PNMR is also described in A.O.C.S. Official Method Cd. 16-81, *Official Methods and Recommended Practices of The American Oil Chemists Society.* 3rd. Ed., 1987 (herein incorporated by reference).

The slope of the SFC profile is calculated by subtracting the percent solids at 70° F. from the percent solids at 98.6° F. and dividing that value by 28.6.

(b). Consistency

The Consistency (K) of the nondigestible oil is measured at a temperature between 20° and 40° C. using a Rheometrics controlled stress rheometer equipped with a cone and plate measuring system. The cone diameter is 4 cm and the cone angle is 2 degrees. A sample of the nondigestible oil is carefully applied to the plate and the cone is then slowly lowered onto the sample (gap=0.048 mm). A flow measurement is performed via the programmed application of a shear stress over time. The shear stress is increased from zero to 5,000 dynes/cm$^2$ over a 2 minutes time span. The applied stress results in deformation of the sample (i.e., strain) and the rate of strain is reported as a shear rate. These data are used to create a flow curve of log [apparent viscosity] versus log [shear rate] for the nondigestible oil sample. The flow curve is then modeled according to the following power law model:

$$\text{Apparent Viscosity} = K\,(\text{Shear Rate})^{n-1}$$

where the apparent viscosity is expressed in units of poise (P), shear rate is in units of 1/sec, K is the Consistency in units of P.sec$^{(n-1)}$, and n is the shear index (dimensionless). The power law model is widely used to describe the flow behavior of non-newtonian materials. On the log-log plot of apparent viscosity versus shear rate, the power law model is a straight line with slope of (n-1). The shear index (n) varies from 0 to 1. The closer n is to 1, the closer the material's flow behavior is to newtonian behavior. The Consistency (K) is numerically equal to the apparent viscosity at a shear rate of 1 sec$^{-1}$. The values of K and n describe the flow behavior of the nondigestible oil within specific limits of shear Before determining Solid Fat Content (SFC values, a sample of the flowable composition or mixture of nondigestible liquid/solid is heated to a temperature of 140° F. (60° C.) or higher for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; and at 32° F. (0° C.) for 15 minutes. After tempering, the SFC values of the sample at temperatures of 50° F. (10° C.), 70° F. (21.1° C.), 80° F. (26.7° C.), 92° F. (33.3° C.) and 98.6° F. (37° C.), can be determined by pulsed nuclear magnetic resonance (PNMR) after equilibration for 30 minutes at each temperature. The method for determining SFC values by PNMR is described in Madison and Hill, *J. Amer. Oil Chem. Soc.,* Vol. 55 (1978), pp. 328-31 (herein incorporated by reference). Measurement of SFC by PNMR is also described in A.O.C.S. Official Method Cd. 16-81, *Official Methods and Recommended Practices of The American Oil Chemists Society.* 3rd. Ed., 1987 (herein incorporated by reference).

The slope of the SFC profile is calculated by subtracting the percent solids at 70° F. from the percent solids at 98.6° F. and dividing that value by 28.6.

(c). Crystallization Onset Temperature

The crystallization onset temperature is that temperature at which, under the conditions of this test, turbidity is induced in the sample within 90 minutes after reaching and maintaining the crystallization onset temperature. Turbidity is caused by the first stage of crystallization.

Apparatus:

1. Jacketed, agitated, cylindrical glass flask, 4 inches in diameter, at least 250 ml volume. Heating and cooling are accomplished by circulation of a clear, uncolored fluid through the jacket. Acceptable jacket fluids are, but are not limited to, water, ethylene glycol, or silicone fluids.
2. Thermometer, calibrated in the range 25° C. to 100° C.

Procedure:

1. In the flask, heat at least 250 ml of sample (but not more than 700 ml) to 85° C. and hold until all solids have dissolved. Before proceeding, the solution must be clear, without any turbidity.
2. Agitate to maintain uniform temperature throughout the flask.
3. Cool at no more than 2.5° C./min to a temperature in the vicinity of the crystallization onset temperature. Note: To prevent crystallization on the vessel walls during cooling, the jacket temperature should never be any colder than 5° C. below the sample temperature.
4. Hold at this temperature for 90 minutes or until the clear solution shows (by viewing horizontally through the vessel wall) the first hint of turbidity.

5. If the solution becomes turbid within 90 minutes, repeat by heating and redissolving the sample as in step 1. Repeat steps 2, 3, and 4, except cool to a temperature 2° C. above the previous measurement.
6. Repeat until the solution does not become turbid within 90 minutes of reaching the test temperature. The crystallization onset temperature is the highest temperature at which the solution becomes turbid within 90 minutes.
7. If, on the first measurement, after 90 minutes the solution remains clear, repeat by heating and redissolving the sample as in step 1. Repeat steps 2, 3, and 4, except cool to a temperature 2° C. below the previous measurement. The crystallization onset temperature is the highest temperature at which the solution becomes turbid within 90 minutes.

(d). Fatty Acid Composition of Polyol Polyesters

The fatty acid composition (FAC) of the polyol polyesters is determined by gas chromatography, using a Hewlett-Packard Model S712A gas chromatograph equipped with a flame ionization detector and a Hewlett-Packard Model 17671A automatic sampler. The chromatographic method used is described in *Official Methods and Recommended Practices of the American Oil Chemists Society*, 3rd Ed., 1984, Procedure I-Ce62 (incorporated herein by reference).

(e). Ester Distribution of Sucrose Polyesters

The relative distribution of the individual octa-, hepta-, hexa- and penta- esters, as well as collectively the tetra-through mono-esters, of the sucrose polyesters can be determined using normal-phase high performance liquid chromatography (HPLC). A silica gel-packed column is used in this method to separate the polyester sample into the respective ester groupings noted above. Hexane and methyl-t-butyl ether are used as the mobile phase solvents. The ester groupings are quantitated using a mass detector (i.e. an evaporative light-scattering detector). The detector response is measured and then normalized to 100%. The individual ester groups are expressed as a relative percentage.

(f). Solid Saturated Polyol Polyester (HPLC)

(a) Solvents: Acetonitrile (ACN), Methylene Chloride and Ethylene Dichloride, all UV grade.
(b) Sample preparation: Weigh 0.1 g into a 10 mL volumetric flask. Dilute to volume with 50/50 (v/v) methylene chloride/ethylene dichloride.
(c) LC system: Model HP1090 with binary or ternary DR5 delivery system, autosampler and heated column compartment (Hewlett Packard, Avondale, Pa.); Rheodyne inline filter (0.5 um), 2 Beckman Ultrasphere analytical columns, 5 um, 25 cm×4.8 mm. Operating conditions: Flow rate, 1.5 mL/min; injection volume, 20 uL; Column temperature, 45° C.; Stop time, 70 min; Post time, 10 min; Solvent program, (A-Acetonitrile, B-50/50 (v%/v%) Methylene Chloride/Ethylene Dichloride): 0 min, 68% B; 15 min, 70% B; 50 min, 77% B; 60 min, 100% B; 70 min, 100% B.
(d) Detector: Applied Chromatography Systems Model #750/14 Evaporative light scattering detector. Operating conditions: Nebulizer gas pressure, 15 psi (nitrogen); Evaporator setting, 60; Attenuation, 2; Photomultiplier, 2; Time constraint, 5.
(e) Data Acquisition: Analog data output from the LC detector is transmitted through a Hewlett Packard 18542A Analog to Digital converter to a Hewlett Packard 1000 computer where data are integrated using Hewlett Packard Laboratory Automation System (LAS rev.D.01) software.
(f) Calculations: Plot sample chromatograms from 15 to 70 minutes. Determine relative peak quantities through area normalization.

(g). Complete Melt Point

Equipment:
Perkin-Elmer 7 Series Thermal Analysis System, Model DSC7, manufactured by Perkin-Elmer, Norwalk, Conn.

Procedure:
1) Sample of polyol polyester is heated to at least 10° C. above the temperature at which all visible solids are melted, and mixed thoroughly.
2) 10±2 mg. of sample is weighed into sample pan.
3) A scan is performed from about 10° C. above the temperature at which all visible solids are melted, to −60° C. at 5° C. per minute.
4) The temperature of the sample is maintained at −60° C. for 3 minutes and scanned from −60° C. to the original starting temperature at 5° C. per minute (i.e. about 10° C. above the temperature at which all visible solids are melted).
5) The complete melting point is the temperature at the intersection of the baseline (i.e., specific heat line) with the line tangent to the trailing edge of the last (highest temperature) endothermic peak.

(h). Thickness of Solid Polyol Fatty Acid Polyester Particles (Light Microscopy)

The thickness of the solid polyol polyester particles formed in the flowable nondigestible oil compositions herein may estimated at room temperature with a Nikon Microphot video-enhanced light microscope (VELM) using Hoffman Modulation Contrast (HMC) optics according to the following method:
1. A small portion (i.e., 1-10 mg) of the nondigestible oil sample with the solid polyol fatty acid polyester particles dispersed therein is placed on a microscope slide and covered. The slide is placed under the microscope.
2. The sample is examined using a HMC 100× oil objective as the standard lens in conjunction with a 10× eyepiece lens.
3. A microscope-mounted video camera and associated controller are used for video enhancement to facilitate differentiation between the sample and the background.
4. The thickness of the solid polyol fatty acid polyester particles is measured in um (microns).

This method permits differentiation of particles having thicknesses just within the resolution of the VELM (approximately 0.2-0.5 um). Particle thickness of particles having smaller dimensions can be determined by the Freeze Fracture Method described hereinafter. (Note: No special sample preparation is required, other than obtaining a representative sample. The samples should be melted and cooled ambiently.) Reference: Robert Hoffman, "The Modulation Contrast Microscope: Principles and Performances", *Journal of Microscopy*, Vol. 110, Pt 3, August 1977, pp. 205-222.

(i). Thickness of Solid Polyol Fatty Acid Polyester Particles (Freeze Fracture Transmission Electron Microscopy)

The three-dimensional topography of particles of polyol fatty acid polyesters and their size can be determined by a freeze-fracture transmission electron microscopy (ff-tem) method. This freeze-fracture method is carried out as follows:
1. The outside cavity of a freezing container is filled with liquid $N_2$ and the inner dewar of the freezing container is filled with liquid ethane (normal melting temperature of −172° C.). The ethane is allowed to freeze.

2. A small amount (1-2 ul) of the nondigestible fat sample with the solid polyol fatty acid polyester particles dispersed therein is placed in the well of a gold-plated Balzers specimen holder. (Note: for very fluid samples, 1-2 ul of sample is placed on a gold planchet (Balzers) and another planchet is placed on top of the first to form a sandwich.)
3. Most of the frozen ethane in the dewar is melted by inserting a metal heat sink into the dewar.
4. Immediately after melting the ethane, the specimen holder containing the nondigestible fat sample is picked up using a pair of tweezers and rapidly plunged into the liquid ethane.
5. After a few seconds, the specimen holder is removed from the ethane, quickly touched to the tip of a camel's hair brush to remove excess ethane, and immediately immersed in the liquid $N_2$ to keep the sample cold.
6. The sample is transferred under liquid $N^2$ to a JEOL JFD-9000C sample holder and then transferred into the chamber of a JEOL JFD-9000C freeze-fracture unit. The temperature of the unit should be about −175° C. Vacuum should be at least $8 \times 10^{-7}$ torr.
7. A knife is cooled to a temperature of about −165° C.
8. The sample is fractured in the JEOL chamber using the pre-cooled knife.
9. Platinum-carbon is deposited onto the fractured sample at a 45° angle for 4.5 seconds, followed by carbon deposition at a 90° angle for 25 seconds to form a replica of the fractured sample. The high voltage is 2500V and the current is 70 mA.
10. The samples are removed from the freeze fracture unit and cleaned using 3 washes of chloroform.
11. The replica is picked up on a 300 mesh copper EM grid and examined in a transmission electron microscope.
12. Images are recorded on negative film and positive prints are made from the negatives.
13. The thickness of the polyol fatty acid polyester particles is measured in nm.

REFERENCES

Rash, J. E. and Hudson, C. S., *Freeze Fracture: Methods, Artifacts, and Interpretations,* New Haven Press, New York, 1979.

Stolinski and Breathnach, *Freeze Fracture Replication of Biological Tissues,* Academic Press, London, 1975.

Steinbrecht and Zierold, *Cryotechniques in Biological Electron Microscopy,* Springer-Verlag, Berlin, 1987.

SPECIFIC EXAMPLES

Preparation of flowable nondigestible fat compositions of the present invention is illustrated by the following examples.

Example I

Preparation of a Flowable Nondigestible Oil containing Solid Polyol Fatty Acid Polyester (comprising a blend of Solid Saturated Polyol Polyester and Solid Diversely Esterified Polyol Polyester)

The above ingredients have the following compositions (% wt):

|  | Solid Polyol Fatty Acid Polyester (%) | Liquid Polyol Fatty Acid Polyester (%) |
| --- | --- | --- |
| Fatty Acid Composition |  |  |
| C8 | — | — |
| C10 | — | — |
| C12 | 0 | — |
| C14 | 0 | — |
| C16 | 1.2 | 9.7 |
| C17 | 0 | 0.1 |
| C18 | 4.6 | 5.9 |
| C18:1 | 3.7 | 64.5 |
| C18:2 | 10.9 | 18.9 |
| C18:3 | 0 | 0.2 |
| C20 | 4.6 | 0.3 |
| C22 | 71.7 | 0.2 |
| C22:1 | 0.2 | — |
| C24 | 2.8 | — |
| Other | 0.4 | 0.2 |
| Ester Distribution |  |  |
| Octa | 71.6 | 78.7 |
| Hepta | 28.2 | 21.0 |
| Hexa | 0.2 | 0.2 |
| Penta | <0.1 | 0.02 |
| Lower | <0.1 | 0.1 |

The solid polyol fatty acid polyester contains about 30 parts solid saturated polyol polyester and about 70 parts solid diversely esterified polyol polyester. The solid and liquid polyol polyester ingredients are mixed at a proportion of 6 weight parts of the solid polyol fatty acid polyester to 94 weight parts of the liquid polyol fatty acid polyester, and agitated to a molten liquid state at a temperature of about 85° C. in a temperature-controlled reactor with agitation. The solid polyesters completely dissolve by 75° C. The reactor is a 4-inch diameter, fully enclosed 1.8-liter cylindrical jacketed glass reactor, with a dish-shaped bottom with bottom-valve discharge, and a magnetic-drive overhead anchor agitator turning at 100 RPM throughout the procedure. The temperature of the reactor contents is cooled to 59° C. (first crystallization temperature) and held at this temperature for 85 minutes. The contents, transparent in the molten state, became increasingly clouded. The reactor contents were then cooled from 59° C. to an ambient temperature of 25° C. (second crystallization temperature) over an 80 minute time period, at a constant 0.43° C./min. cooling rate. The flowable nondigestible oil product was drained from the bottom of the reactor at 25° C., with all but a thin film of the material remaining attached to the inside walls and the agitator.

The final flowable nondigestible oil product has the following physical attributes:

Shear index: n=0.8

Consistency (25° C.): 50.0 $P.sec^{(n-1)}$.

The same nondigestible oil material, if rapidly cooled quiescently (without shear) from its molten state (80° C.) to an ambient temperature of 25° C. at a rate of at least 0.5° C./min, will yield a stiffened, nonflowable composition with a Consistency at 25° C. of about 800 $P.sec^{(n-1)}$ and a shear index of about 0.2-0.3.

Example II

The procedure of Example I is repeated wherein the solid polyol fatty acid polyester and the liquid polyol polyester are mixed in a proportion of 6.95 parts to 93.05 parts. The compositions were cooled from 85° C. to the onset crystallization temperatures shown below in the range of 63° C. to about 57° C., and were held at that temperatures for the time period shown. The compositions were then cooled to 25° C. at a cooling rate of about 0.5° C. per minute. The resulting composition were then analyzed for flowability in terms of Consistency.

| Hold Temperature | Hold Time min | Consistency k P.sec$^{(n-1)}$ | Shear Index n | Shear Range 1/sec |
|---|---|---|---|---|
| 63° C. | No crystals after stirring 90 minutes | | | |
| 61° C. | 45 | 1200 | 0.2 | 2.0-50 |
| | 90 | 483 | 0.4 | 2.0-150 |
| 59° C. | 5 | 140 | 0.7 | 2.0-50 |
| | 15 | 56 | 0.8 | 2.0-500 |
| | 30 | 53 | 0.8 | 2.0-150 |
| | 45 | 53 | 0.8 | 2.0-150 |
| 57° C. | 15 | 1190 | 0.2 | 2.0-70 |
| | 30 | 540 | 0.4 | 2.0-450 |
| | 45 | 310 | 0.5 | 2.0-20 |

What is claimed is:

1. A flowable nondigestible oil composition comprising a liquid polyol fatty acid polyester having a complete melt point less than 37° C., and a crystallized solid polyol fatty acid polyester having a complete melt point of at least about 37° C., said solid polyol fatty acid polyester comprising a plurality of crystallized spherulites comprising a solid saturated polyol polyester within the liquid polyol fatty acid polyester, wherein particles of said crystallized solid polyol fatty acid polyester have a diameter of from about 1 microns to about 50 microns, and wherein the flowable nondigestible oil composition has a Consistency in a temperature range of 20-40° C. in the range of from about 0 P.sec$^{(n-1)}$ to about 30 P.sec$^{(n-1)}$, and wherein the solid polyol fatty acid polyester is crystallized while shearing the nondigestible oil.

2. The flowable composition according to claim 1 wherein the crystallized solid polyol fatty acid polyester further comprises a plurality of crystallized aggregated spherulites comprising a core comprising a solid saturated polyol polyester, and surrounded by crystallized aggregate particles crystallized to the spherulite comprising a solid diversely esterified polyol polyester.

3. The flowable composition according to claim 2 wherein the solid polyol fatty acid polyester is crystallized in less than about 2 hours.

4. The flowable nondigestible oil composition according to claim 2 wherein the Consistency in a temperature range of 20°-40° C. is in the range of from about 0 P.sec$^{(n-1)}$ to about 20 P.sec$^{(n-1)}$.

5. The flowable nondigestible oil composition according to claim 4 wherein the Consistency in a temperature range of 20°-40° C. is in the range of from about 0 P.sec$^{(n-1)}$ to about 10 P.sec$^{(n-1)}$.

6. The flowable nondigestible oil composition according to claim 2 wherein solid saturated polyol polyester is selected from hepta-substituted saturated fatty acid polyol polyester, octa-substituted saturated fatty acid polyol polyester, and mixtures thereof, having C20-C24 saturated fatty acid radicals, and wherein the solid diversely esterified polyol polyester is selected from hepta-substituted diversely esterified polyol polyester, octa-substituted diversely esterified polyol polyester, and mixtures thereof, having fatty acid radicals comprising a) long chain saturated fatty acid radicals, and b) dissimilar fatty acid radicals which are dissimilar from the long chain saturated fatty acid radicals and are selected from the group consisting of i) long chain unsaturated fatty acid radicals, ii) short chain saturated fatty acid radicals, and iii) mixtures thereof.

7. The flowable nondigestible oil composition according to claim 6 wherein the solid saturated polyol polyester comprises at least 5% by weight sucrose octasaturate.

8. The flowable nondigestible oil composition according to claim 6 wherein the crystallized aggregated spherulites have a maximum dimension of from about 3 microns to about 32 microns.

9. The flowable nondigestible oil composition according to claim 6 further comprising temperature-sensitive food additives.

10. The flowable nondigestible oil composition according to claim 6 wherein the solid saturated polyol polyester comprises octa-behenate sucrose polyester, and wherein the solid diversely esterified polyol polyester comprises sucrose polyester wherein the esters are selected from behenate and a mixture of oleate and linoleate.

11. The flowable nondigestible oil composition according to claim 6 wherein the solid polyol fatty acid polyester has fatty acid esters comprising long chain saturated fatty acid esters and long chain unsaturated fatty acid esters in a ratio thereof of from 5:3 to about 7:1.

12. The flowable nondigestible oil composition according to claim 11 wherein the ratio of long chain saturated fatty acid esters to long chain unsaturated fatty acid esters is from about 6:2 to about 6.5:1.5.

13. The flowable composition according to claim 1 wherein the solid polyol fatty acid polyester further comprises aggregate particles comprising the solid diversely esterified polyol polyester.

14. The flowable nondigestible oil composition of claim 1 comprising, by weight, 50-99% of the liquid polyol fatty acid polyester, and 1-50% of the solid polyol fatty acid polyester.

15. The flowable nondigestible oil composition according to claim 1 wherein the Consistency in a temperature range of 20°-40° C. is in the range of from about 0 P.sec$^{(n-1)}$ to about 25 P.sec$^{(n-1)}$.

16. The flowable nondigestible oil composition according to claim 15 wherein the Consistency in a temperature range of 20°-40° C. is in the range of from about 0 P.sec$^{(n-1)}$ to about 20 P.sec$^{(n-1)}$.

17. The flowable nondigestible oil composition according to claim 16 wherein the Consistency in a temperature range of 20°-40° C. is in the range of from about 0 P.sec$^{(n-1)}$ to about 10 P.sec$^{(n-1)}$.

18. The flowable nondigestible oil composition according to claim 1 wherein the solid saturated polyol polyester has a complete melt point of at least about 60° C.

19. A flowable nondigestible oil composition comprising a liquid polyol fatty acid polyester having a complete melt point less than 37° C., and a crystallized solid polyol fatty acid polyester having a complete melt point of at least about 37° C., said solid polyol fatty acid polyester comprising a plurality of crystallized spherulites comprising a solid saturated polyol polyester within the liquid polyol fatty acid polyester, wherein particles of said crystallized solid polyol fatty acid polyester have a diameter of from about 1 microns to about 50 microns, and wherein the flowable nondigestible oil composition has a Consistency in a temperature range of 20-40° C. in the range of from about 0 P.sec$^{(n-1)}$ to about 30 P.sec$^{(n-1)}$, and wherein the solid polyol fatty acid polyester is crystallized in less than about 5 hours.

20. A flowable nondigestible oil composition comprising a liquid polyol fatty acid polyester having a complete melt point of a less than about 37° C., and a solid polyol fatty acid polyester having a complete melt point of at least about 37° C., wherein the solid polyol fatty acid polyester is in the form of crystallized spherulitic particles, wherein said crystallized spherulitic particles have a diameter of from about 1 microns to about 50 microns, and wherein the flowable nondigestible oil composition has a Consistency in a temperature range of 20-40° C. in the range of from about 0 $P.sec^{(n-1)}$ to about 30 $P.sec^{(n-1)}$.

21. The flowable nondigestible oil composition according to claim 20 wherein the Consistency is in the range of from about 0 $P.sec^{(n-1)}$ to about 25 $P.sec^{(n-1)}$.

22. The flowable nondigestible oil composition according to claim 20 wherein the solid polyol fatty acid polyester is selected from the group consisting of (i) a solid saturated polyol polyester and (ii) combinations of solid saturated polyol polyester with a solid diversely esterified polyol polyester; a polyol polyester polymer; or combinations of said diversely esterified polyol polyester and said solid polyester polymer.

23. The flowable nondigestible oil composition according to claim 22 wherein solid polyol fatty acid polyester comprises a solid saturated polyol polyester and a solid diversely esterified polyol polyester.

24. The flowable nondigestible oil composition according to claim 23 wherein the solid saturated polyol polyester and the solid diversely esterified polyol polyester are in the form of co-crystallized particles.

25. The flowable nondigestible oil composition according to claim 23 wherein solid saturated polyol polyester is selected from hepta-substituted saturated fatty acid polyol polyester, octa-substituted saturated fatty acid polyol polyester, and mixtures thereof, having $C_{20}$-$C_{24}$ saturated fatty acid ester moieties, and wherein the solid diversely esterified polyol polyester is selected from hepta-substituted diversely esterified polyol polyesters, octa-substituted diversely esterified polyol polyesters, and mixtures thereof, having fatty acid ester moieties comprising a) long chain saturated fatty acid ester moieties, and b) dissimilar fatty acid ester moieties which are dissimilar from the long chain saturated fatty acid ester moieties and are selected from the group consisting of i) long chain unsaturated fatty acid ester moieties, ii) short chain saturated fatty acid ester moieties, and iii) mixtures thereof.

26. The flowable nondigestible oil composition according to claim 25 wherein the solid sucrose polyester comprises at least 5% by weight sucrose octabehenate.

27. The flowable nondigestible oil composition according to claim 25 wherein the solid saturated polyol polyester comprises octa-behenate sucrose polyester, and wherein the solid diversely esterified polyol polyester comprises octa-saturated sucrose polyester wherein the esters are selected from behenate and a mixture of oleate and linoleate.

28. The flowable nondigestible oil composition according to claim 25 wherein the solid polyol fatty acid polyester has fatty acid ester moieties comprising long chain saturated fatty acid ester moieties and long chain unsaturated fatty acid ester moieties in a ratio thereof of from 5:3 to about 7:1.

29. The flowable nondigestible oil composition according to claim 25 wherein the ratio of long chain saturated fatty acid esters to long chain unsaturated fatty acid esters is from about 6:2 to about 6.5:1.5.

30. The flowable nondigestible oil composition according to claim 25 further comprising temperature-sensitive food additives.

31. The flowable nondigestible oil composition of claim 20 comprising, by weight, 50-99% of the liquid polyol fatty acid polyester, and 1-50% of the solid polyol fatty acid polyester.

32. The flowable nondigestible oil composition according to claim 20 wherein the crystallized particles have a maximum dimension of from about 1 micron to about 30 microns.

33. The flowable nondigestible oil composition according to claim 20 wherein the solid sucrose polyester has a complete melt point of at least about 60° C.

* * * * *